(12) United States Patent
Walsh et al.

(10) Patent No.: US 11,976,303 B2
(45) Date of Patent: *May 7, 2024

(54) METHODS FOR NUCLEAR REPROGRAMMING OF CELLS

(71) Applicant: LONZA LTD, Basel (CH)

(72) Inventors: Patrick Walsh, Gaithersburg, MD (US); Thomas Fellner, Gaithersburg, MD (US)

(73) Assignee: LONZA LTD, Basel (CH)

( * ) Notice: Subject to any disclaimer, the term of this patent is extended or adjusted under 35 U.S.C. 154(b) by 708 days.

This patent is subject to a terminal disclaimer.

(21) Appl. No.: 16/994,336

(22) Filed: Aug. 14, 2020

(65) Prior Publication Data

US 2020/0385688 A1  Dec. 10, 2020

Related U.S. Application Data

(63) Continuation of application No. 14/493,107, filed on Sep. 22, 2014, now Pat. No. 10,745,668.

(60) Provisional application No. 61/880,579, filed on Sep. 20, 2013.

(51) Int. Cl.
  *C12N 5/074* (2010.01)
  *A61K 33/08* (2006.01)

(52) U.S. Cl.
  CPC ............ *C12N 5/0696* (2013.01); *A61K 33/08* (2013.01); *C12N 2500/12* (2013.01); *C12N 2500/90* (2013.01); *C12N 2506/11* (2013.01); *C12N 2506/115* (2013.01); *C12N 2533/52* (2013.01)

(58) Field of Classification Search
  CPC .............. C12N 5/0696; C12N 2500/12; C12N 2500/90; C12N 2506/11; C12N 2506/115; C12N 2533/52; C12N 2501/602; C12N 2501/603; C12N 2501/604; C12N 2501/605; C12N 2501/606; C12N 2501/608; A61K 33/08; A61P 1/04; A61P 3/10; A61P 7/00; A61P 7/06; A61P 9/10; A61P 11/06; A61P 17/00; A61P 19/00; A61P 19/02; A61P 19/10; A61P 25/00; A61P 25/16; A61P 25/28; A61P 29/00; A61P 35/02; A61P 37/06

See application file for complete search history.

(56) References Cited

U.S. PATENT DOCUMENTS

| | | |
|---|---|---|
| 2003/0022831 A1 | 1/2003 | Rothbard et al. |
| 2003/0032593 A1 | 2/2003 | Wender et al. |
| 2003/0083256 A1 | 5/2003 | Rothbard et al. |
| 2003/0220334 A1 | 11/2003 | Wender et al. |

FOREIGN PATENT DOCUMENTS

| | | |
|---|---|---|
| CN | 101492676 A | 7/2009 |
| CN | 102093981 A | 6/2011 |
| CN | 102115760 A | 7/2011 |
| CN | 1446227 B | 10/2011 |
| CN | 102317448 B | 11/2014 |
| CN | 102725409 B | 3/2016 |
| WO | 2008/008923 A2 | 1/2008 |
| WO | 2010/033920 A2 | 3/2010 |
| WO | 2012/079278 A1 | 6/2012 |
| WO | 2012/112458 A2 | 8/2012 |
| WO | 2013/109763 A2 | 7/2013 |

OTHER PUBLICATIONS

Hogenesch et al, Mechanism of immunopotentiation and saftey of aluminium adjuvants, frontiers in Immunology, 3(406): 1-13, 2013. (Year: 2013).*
Yamasaki et al, Generation of Human Induced Pluripotent Stem (iPS) Cells in Serum- and Feeder-Free Defined Culture and TGF-b1 Regulation of Pluripotency, PLOS one, vol. 9, Issue 1, 2014. (Year: 2014).*
Pessosa et al, Induced pluripotent stem cells throughout the animal kingdom: Availability and applications, World J Stem Cells Aug. 26, 2019; 11(8): 491-505 (Year: 2019).*
Lim et al, Somatic cell transformation into stem cell-like cells induced by different microenvironments, Organogenesis, 9:4, 245-248, 2013 (Year: 2013).*
Bondy, S., "The neurotoxicity of environmental aluminum is still an issue", NeuroToxicity, (2010) 31:575-581.
Brevini, T.A.L, et al., "No shortcuts to pig embryonic stem cells", Theriogenology, (2010) 74:554-550.
Campbell, A., et al., "Differential Toxicity of Aluminum Salts in Human Cell Lines of Neural Origin: Implications for Neurodegeneration", NeuroToxicology, (2001) 22:63-71.
Chou, B-K., et al., "Efficient human iPS cell derivation by a non-integrating plasmid from blood cells with unique epigenetic and gene expression signatures", Cell Research, (2011) 21:518-529.
Futaki, S., et al., "Structural variety of membrane permeable peptides", Curr. Protein Pept. Sci., (2003) 4(2):87-96.
Hogenesche, H., et al., "Mechanism of immunopotentiation and safety of aluminum adjuvants", Frontiers in Immunol., (2013) 3(406):1-13.

(Continued)

*Primary Examiner* — Emily A Cordas
*Assistant Examiner* — Constantina E Stavrou
(74) *Attorney, Agent, or Firm* — MEDLER FERRO WOODHOUSE & MILLS PLLC

(57) ABSTRACT

Described herein are methods for enhancing the nuclear reprogramming of somatic cells to become induced pluripotent stem cells. In particular, the methods disclosed herein involve the use of damage-associated molecular pattern molecules (DAMP). In certain embodiments the DAMPs are aluminum compositions such as aluminum hydroxide. Such DAMPs have unexpectedly and surprisingly been found to enhance the nuclear reprogramming efficiency of the reprogramming factors commonly used to induce somatic cells to become induced pluripotent stem cells. Accordingly, this disclosure describes methods of nuclear reprogramming as well as cells obtained from such methods along with therapeutic methods for using such cells for the treatment of disease amendable to treatment by stem cell therapy; as well as kits for such uses.

14 Claims, 5 Drawing Sheets

Specification includes a Sequence Listing.

(56) References Cited

OTHER PUBLICATIONS

Huangfu, D., et al., "Induction of pluripotent stem cells by defined factors is greatly improved by small-molecule compounds", Nature Biotechnol., (2008) 26(7):795-797.

Ieda, M., et al., "Direct Reprogramming of Fibroblasts into Functional Cardiomyocytes by Defined Factors", Cell, (2010) 142:375-386.

International Search Report and the Written Opinion of the International Searching Authority for International Application No. PCT/IB2014/002816, mailed Jun. 8, 2015.

Lee, J., et al., "Activation of Innate Immunity is Required for Efficient Nuclear Reprogramming", Cell, (2012) 151(3):547-558.

Li, H., et al., "Aluminum Hydroxide Adjuvants Activate Caspase-1 and Induce IL-1β and IL-18 Release", J. Immunol, (2007) 178:5271-5276.

Liu, T., et al. "High Efficiency Reprogramming CD34+ Cells Derived from Human Amniotic Fluid into Induced Pluripotent Stem Cells with Oct. 14", Stem Cells and Development, (2012) 21:2322-2332.

Marichal, T., et al., "DNA released from dying host cells mediates aluminum adjuvant activity", Nature Medicine, (2011) 17(8):996-1003.

Munoz, M., et al., "Conventional pluripotency markers are unspecific for bovine embryonic-derived cell-lines", Theriogenology, (2008) 69:1159-1164.

Ohmine, S., et al., "Induced pluripotent stem cells from GMP-grade hematopoietic progenitor cells and mononuclear myeloid cells", Stem Cell Res. Ther., (2011) 2:1-2.

Okita, K., et al., "An Efficient Nonviral Method to Generate Integration-Free Human-Induced Pluripotent Stem Cells from Cord Blood and Peripheral Blood Cells", Stem Cells, (2013) 31:458-466.

Omole, A.E., et al., "Ten years of progress and promise of induced pluripotent stem cells: historical origins, characteristics, mechanisms, limitations, and potential applications", PeerJ, (2018) 6:1-47.

Paris, D.B.B.P., et al., "Equine embryos and embryonic stem cells: Defining reliable markers of pluripotency", Theriogenology, (2010) 74:516-524.

Petrovsky, N., "Comparative safety of vaccine adjuvants: a summary of current evidence and future needs", Drug Saf., (2015) 38(11):1059-1074.

Reinhardt, C.A., et al., "Cell Detachment and Growth of Fibroblasts as Parameters for Cytotoxicity of Inorganic Metal Salts In Vitro", Cell Biology and Toxicology, (1985) 1(2):33-43.

Sayed, N., et al., "Activation of Innate Immunity is Required for Efficient Nuclear Reprogramming and Endothelial Differentiation", Circulation (2012) 126(suppl. 21):Abstract 17896.

Shakeri, S., et al., "Aluminum Phosphide Poisoning in Animals", Int. J. Med Toxicol. Forensic Med., (2015) 5(2):81-97.

Shi, Y., et al. "Induction of Pluripotent Stem Cells from Mouse Embryonic Fibroblasts by Oct4 and Klf4 with Small-Molecule Compounds", Cell Stem Cell, (2008) 3:568-574.

Uemura, S., et al., "Short Polymers of Arginine Rapidly Translocate Into Vascular Cells: Effects on Nitric Oxide Synthesis", Circ. J., (2002) 66:1155-1160.

Violante, A., et al., "Formation Mechanism of Aluminum Hydroxide Polymorphs", Clays and Clay Minerals, (1993) 41(5):590-597.

Wender, P.A., et al., "The design, synthesis, and evaluation of molecules that enable or enhance cellular uptake: Peptoid molecular transporters", Proc. Natl. Acad. Sci. USA, (2000) 97(24):13003-13008.

Yamanaka, S., "A Fresh Look at iPS Cells", Cell, (2009) 137:13-17.

Yamanaka, S., et al., "Nuclear reprogramming to a pluripotent state by three approaches", Nature, (2010) 465:704-710.

Zhou, H., et al. "Generation of induced pluripotent stem cells using recombinant proteins", Cell Stem Cell, (2009) 4(5): 381-384.

\* cited by examiner

SEQUENCE LISTING

```
<160> NUMBER OF SEQ ID NOS: 15

<210> SEQ ID NO 1
<211> LENGTH: 479
<212> TYPE: PRT
<213> ORGANISM: Homo sapiens

<400> SEQUENCE: 1

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125
```

```
Ser Ala Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
                180                 185                 190

Val Ser Pro Ser Gly Gly Phe Val Ala Glu Leu Leu Arg Pro Glu Leu
            195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
                260                 265                 270

Thr Cys Pro Lys Ile Lys Gln Glu Ala Val Ser Ser Cys Thr His Leu
            275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
                340                 345                 350

Pro Asp Gln Met Gln Pro Gln Val Pro Pro Leu His Tyr Gln Glu Leu
            355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
    435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 2
<211> LENGTH: 2949
<212> TYPE: DNA
<213> ORGANISM: Homo sapiens

<400> SEQUENCE: 2
agtttcccga ccagagagaa cgaacgtgtc tgcgggcgcg cggggagcag aggcggtggc    60
gggcggcggc ggcaccggga gccgccgagt gaccctcccc cgcccctctg gcccccacc    120 ctcccacccg cccgtggccc gcgcccatgg ccgcgcgcgc tccacacaac tcaccggagt    180
```

```
ccgcgccttg cgccgccgac cagttcgcag ctccgcgcca cggcagccag tctcacctgg     240
cggcaccgcc cgcccaccgc cccggccaca gcccctgcgc ccacggcagc actcgaggcg     300
accgcgacag tggtggggga cgctgctgag tggaagagag cgcagccgg ccaccggacc      360 tacttactcg ccttgctgat tgtctatttt tgcgtttaca acttttctaa gaacttttgt     420
atacaaagga acttttttaaa aaagacgctt ccaagttata tttaatccaa agaagaagga    480
tctcggccaa tttggggttt tgggttttgg cttcgtttct tctcttcgtt gactttgggg     540
ttcaggtgcc ccagctgctt cgggctgccg aggaccttct ggcccccac attaatgagg      600 cagccacctg gcgagtctga catggctgtc agcgacgcgc tgctcccatc tttctccacg     660
ttcgcgtctg gcccggcggg aagggagaag acactgcgtc aagcaggtgc cccgaataac     720
cgctggcgga aggagctctc ccacatgaag cgacttcccc cagtgcttcc cggccgcccc    780
tatgacctgg cggcggcgac cgtggccaca gacctggaga gcggcggagc cggtgcggct     840
tgcggcggta gcaacctggc gcccctacct cggagagaga ccgaggagtt caacgatctc     900
ctggacctgg actttattct ctccaattcg ctgacccatc ctccggagtc agtggccgcc     960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagcccct cggcgggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagcccctg acggcagcca cccggtggtg   1380
gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtcccgccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgaa attcgcccg ctcagatgaa     1920 ctgaccaggc actaccgtaa acacacgggg caccgcccgt tccagtgcca aaaatgcgac   1980
cgagcatttt ccaggtcgga ccacctcgcc ttacacatga gaggcatttt ttaaatccca   2040
gacagtggat atgacccaca ctgccagaag agaattcagt attttttact tttcacactg   2100
tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaaggggggt gactggaagt tgtggatatc agggtataaa   2340
ttatatccgt gagttggggg agggaagacc agaattccct tgaattgtgt attgatgcaa   2400
tataagcata aagatcacc ttgtattctc tttaccttct aaaagccatt attatgatgt      2460
tagaagaaga ggaagaaatt caggtacaga aaacatgttt aaatagccta aatgatggtg   2520
```

-continued

```
cttggtgagt cttggttcta aaggtaccaa acaaggaagc caaagttttc aaactgctgc    2580
atactttgac aaggaaaatc tatatttgtc ttccgatcaa catttatgac ctaagtcagg    2640
taatatacct ggtttacttc tttagcattt ttatgcagac agtctgttat gcactgtggt    2700
ttcagatgtg caataatttg tacaatggtt tattcccaag tatgccttaa gcagaacaaa    2760 tgtgttttc tatatagttc cttgccttaa taaatatgta atataaattt aagcaaacgt     2820
ctattttgta tatttgtaaa ctacaaagta aaatgaacat tttgtggagt ttgtattttg    2880
catactcaag gtgagaatta agttttaaat aaacctataa tatttatct gaaaaaaaaa     2940 aaaaaaaaa                                                            2949
```

<210> SEQ ID NO 3
<211> LENGTH: 454
<212> TYPE: PRT
<213> ORGANISM: Homo sapiens

<400> SEQUENCE: 3

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
```

```
        290                 295                 300
Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 4
<211> LENGTH: 2379
<212> TYPE: DNA
<213> ORGANISM: Homo sapiens

<400> SEQUENCE: 4
gacccccgag ctgtgctgct cgcggccgcc accgccgggc cccggccgtc cctggctccc      60
ctcctgcctc gagaagggca gggcttctca gaggcttggc gggaaaaaga acggagggag     120
ggatcgcgct gagtataaaa gccggttttc ggggctttat ctaactcgct gtagtaattc     180
cagcgagagg cagagggagc gagcgggcgg ccggctaggg tggaagagcc gggcgagcag     240
agctgcgctg cgggcgtcct gggaagggag atcggagcg aatagggggc ttcgcctctg      300
gcccagccct cccgctgatc ccccagccag cggtccgcaa ccttgccgc atccacgaaa      360 ctttgcccat agcagcgggc gggcactttg cactggaact acaacacccc agcaaggac      420 gcgactctcc cgacgcgggg aggctattct gcccatttgg ggacacttcc ccgccgctgc     480
caggacccgc ttctctgaaa ggctctcctt gcagctgctt agacgctgga ttttttttcgg   540 gtagtggaaa accagcagcc tcccgcgacg atgccctca acgttagctt caccaacagg      600
aactatgacc tcgactacga ctcggtgcag ccgtatttct actgcgacga ggaggagaac     660
ttctaccagc agcagcagca gagcgagctg cagccccgg cgcccagcga ggatatctgg      720
aagaaattcg agctgctgcc caccccgccc ctgtccccta gccgccgctc cgggctctgc     780
tcgccctcct acgttgcggt cacacccttc tcccttcggg gagacaacga cggcggtggc     840
gggagcttct ccacggccga ccagctggag atggtgaccg agctgctggg aggagacatg     900
gtgaaccaga gtttcatctg cgacccggac gacgagacct tcatcaaaaa catcatcatc     960
caggactgta tgtggagcgg cttctcggcc gccgccaagc tcgtctcaga gaagctggcc    1020
tcctaccagg ctgcgcgcaa agacagcggc agcccgaacc ccgccgcgg ccacagcgtc     1080 tgctccacct ccagcttgta cctgcaggat ctgagcgccg ccgcctcaga gtgcatcgac    1140
ccctcggtgg tcttccccta ccctctcaac gacagcagct cgcccaagtc ctgcgcctcg    1200
```

-continued

```
caagactcca gcgccttctc tccgtcctcg gattctctgc tctcctcgac ggagtcctcc    1260
ccgcagggca gccccgagcc cctggtgctc catgaggaga ccgcccac caccagcagc     1320 gactctgagg aggaacaaga agatgaggaa gaaatcgatg ttgtttctgt ggaaagagg    1380 caggctcctg gcaaaggtc agagtctgga tcaccttctg ctggaggcca cagcaaacct   1440
cctcacagcc cactggtcct caagaggtgc cacgtctcca cacatcagca caactacgca  1500
gcgcctccct ccactcggaa ggactatcct gctgccaaga gggtcaagtt ggacagtgtc   1560
agagtcctga gacagatcag caacaaccga aaatgcacca gccccaggtc ctcggacacc   1620
gaggagaatg tcaagaggcg aacacacaac gtcttggagc gccagaggag gaacgagcta   1680
aaacggagct ttttgccct gcgtgaccag atcccggagt tggaaaacaa tgaaaaggcc    1740
cccaaggtag ttatccttaa aaaagccaca gcatacatcc tgtccgtcca agcagaggag   1800
caaaagctca tttctgaaga ggacttgttg cggaaacgac gagaacagtt gaaacacaaa   1860
cttgaacagc tacggaactc ttgtgcgtaa ggaaaagtaa ggaaaacgat tccttctaac   1920
agaaatgtcc tgagcaatca cctatgaact tgtttcaaat gcatgatcaa atgcaacctc   1980
acaaccttgg ctgagtcttg agactgaaag atttagccat aatgtaaact gcctcaaatt   2040
ggactttggg cataaaagaa ctттттттатg cttaccatct ттттттттттс ttaacagat   2100 ttgtatttaa gaattgtttt taaaaaattt taagatttac acaatgtttc tctgtaaata    2160
ttgccattaa atgtaaataa ctttaataaa acgtttatag cagttacaca gaatttcaat   2220
cctagtatat agtacctagt attataggta ctataaccc taattttttt tattaagta    2280 catttgctt tttaaagttg atttttttct атттgттттта gaaaaaataa aataactggc    2340
aaatatatca ttgagccaaa tcttaaaaaa aaaaaaaaa                          2379
```

<210> SEQ ID NO 5
<211> LENGTH: 305
<212> TYPE: PRT
<213> ORGANISM: Homo sapiens

<400> SEQUENCE: 5

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160
```

```
Asn Ser Asn Gly Val Thr Gln Lys Ala Ser Ala Pro Thr Tyr Pro Ser
            165                 170                 175
Leu Tyr Ser Ser Tyr His Gln Gly Cys Leu Val Asn Pro Thr Gly Asn
        180                 185                 190
Leu Pro Met Trp Ser Asn Gln Thr Trp Asn Asn Ser Thr Trp Ser Asn
            195                 200                 205
Gln Thr Gln Asn Ile Gln Ser Trp Ser Asn His Ser Trp Asn Thr Gln
        210                 215                 220
Thr Trp Cys Thr Gln Ser Trp Asn Asn Gln Ala Trp Asn Ser Pro Phe
225                 230                 235                 240
Tyr Asn Cys Gly Glu Glu Ser Leu Gln Ser Cys Met Gln Phe Gln Pro
                245                 250                 255
Asn Ser Pro Ala Ser Asp Leu Glu Ala Ala Leu Glu Ala Ala Gly Glu
            260                 265                 270
Gly Leu Asn Val Ile Gln Gln Thr Thr Arg Tyr Phe Ser Thr Pro Gln
        275                 280                 285
Thr Met Asp Leu Phe Leu Asn Tyr Ser Met Asn Met Gln Pro Glu Asp
    290                 295                 300
Val
305

<210> SEQ ID NO 6
<211> LENGTH: 2098
<212> TYPE: DNA
<213> ORGANISM: Homo sapiens

<400> SEQUENCE: 6
attataaatc tagagactcc aggattttaa cgttctgctg gactgagctg gttgcctcat      60
gttattatgc aggcaactca ctttatccca atttcttgat acttttcctt ctggaggtcc     120
tatttctcta acatcttcca gaaaagtctt aaagctgcct taacctttt  tccagtccac     180
ctcttaaatt ttttcctcct cttcctctat actaacatga gtgtggatcc agcttgtccc     240
caaagcttgc cttgctttga agcatccgac tgtaaagaat cttcacctat gcctgtgatt     300
tgtgggcctg aagaaaacta tccatccttg caaatgtctt ctgctgagat gcctcacacg     360
gagactgtct ctcctcttcc ttcctccatg gatctgctta ttcaggacag ccctgattct     420
tccaccagtc ccaaaggcaa caacccact  tctgcagaga gagtgtcgc  aaaaaaggaa     480
gacaaggtcc cggtcaagaa acagaagacc agaactgtgt tctcttccac ccagctgtgt     540
gtactcaatg atagatttca gagacagaaa tacctcagcc tccagcagat gcaagaactc     600
tccaacatcc tgaacctcag ctacaaacag gtgaagacct ggttccagaa ccagagaatg     660
aaatctaaga ggtggcagaa aaacaactgg ccgaagaata gcaatggtgt gacgcagaag     720
gcctcagcac ctacctaccc cagcctttac tcttcctacc accagggatg cctggtgaac     780
ccgactggga accttccaat gtggagcaac cagacctgga caattcaac  tggagcaac     840
cagacccaga catccagtc  ctggagcaac cactcctgga cactcagac  ctggtgcacc     900
caatcctgga caatcaggc  ctggaacagt cccttctata ctgtggaga  ggaatctctg     960
cagtcctgca tgcagttcca gccaaattct cctgccagtg acttggaggc tgccttggaa    1020
gctgctgggg aaggccttaa tgtaatacag cagaccacta ggtatttag  tactccacaa    1080
accatggatt tattcctaaa ctactccatg aacatgcaac ctgaagacgt gtgaagatga    1140
gtgaaactga tattactcaa tttcagtctg acactggct  gaatccttcc tctcccctcc    1200
tcccatccct cataggattt tcttgtttg  gaaccacgt  gttctggttt ccatgatgcc    1260
```

```
catccagtca atctcatgga gggtggagta tggttggagc ctaatcagcg aggtttcttt    1320 ttttttttt ttcctattgg atcttcctgg agaaaatact tttttttttt tttttttga      1380 aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctccct    1620
aacagctggg atttacaggc gtgagccacc gcgccctgcc tagaaaagac attttaataa    1680
ccttggctgc cgtctctggc tatagataag tagatctaat actagtttgg atatctttag    1740
ggtttagaat ctaacctcaa gaataagaaa tacaagtaca aattggtgat gaagatgtat    1800
tcgtattgtt tgggattggg aggctttgct tattttttaa aaactattga ggtaaagggt    1860
taagctgtaa catacttaat tgatttctta ccgttttttgg ctctgttttg ctatatcccc   1920
taatttgttg gttgtgctaa tctttgtaga aagaggtctc gtatttgctg catcgtaatg    1980
acatgagtac tgctttagtt ggtttaagtt caaatgaatg aaacaactat ttttccttta    2040
gttgatttta ccctgatttc accgagtgtt tcaatgagta aatatacagc ttaaacat     2098
```

<210> SEQ ID NO 7
<211> LENGTH: 209
<212> TYPE: PRT
<213> ORGANISM: Homo sapiens

<400> SEQUENCE: 7

```
Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn
```

<210> SEQ ID NO 8
<211> LENGTH: 4014
<212> TYPE: DNA
<213> ORGANISM: Homo sapiens

<400> SEQUENCE: 8

```
gtgcggggga agatgtagca gcttcttctc cgaaccaacc ctttgccttc ggacttctcc      60
ggggccagca gccgcccgac caggggcccg ggccacgggg ctcagccgac gaccatgggc     120
tccgtgtcca accagcagtt tgcaggtggc tgcgccaagg cggcagaaga ggcgcccgag     180
gaggcgccgg aggacgcggc ccgggcggcg gacgagcctc agctgctgca cggtgcgggc     240
atctgtaagt ggttcaacgt gcgcatgggg ttcggcttcc tgtccatgac cgcccgcgcc     300
ggggtcgcgc tcgaccccc agtggatgtc tttgtgcacc agagtaagct gcacatggaa      360
gggttccgga gcttgaagga gggtgaggca gtggagttca cctttaagaa gtcagccaag     420
ggtctggaat ccatccgtgt caccggacct ggtggagtat tctgtattgg gagtgagagg     480
cggccaaaag gaaagagcat gcagaagcgc agatcaaaag agacaggtg ctacaactgt       540 ggaggtctag atcatcatgc caaggaatgc aagctgccac cccagcccaa gaagtgccac     600
ttctgccaga gcatcagcca tatggtagcc tcatgtccgc tgaaggccca gcagggccct     660
agtgcacagg gaaagccaac ctactttcga gaggaagaag aagaaatcca cagccctacc     720
ctgctcccgg aggcacagaa ttgagccaca atgggtgggg gctattcttt tgctatcagg     780
aagttttgag gagcaggcag agtggagaaa gtgggaatag ggtgcattgg ggctagttgg     840
cactgccatg tatctcaggc ttgggttcac accatcaccc tttcttccct ctaggtgggg     900
ggaaagggtg agtcaaagga actccaacca tgctctgtcc aaatgcaagt gagggttctg     960
ggggcaacca ggaggggga atcaccctac aacctgcata ctttgagtct ccatccccag     1020
aatttccagc ttttgaaagt ggcctggata gggaagttgt tttcctttta aagaaggata    1080
tataataatt cccatgccag agtgaaatga ttaagtataa gaccagattc atggagccaa    1140
gccactacat tctgtggaag gagatctctc aggagtaagc attgttttt tttcacatct     1200 tgtatcctca tacccacttt tgggataggg tgctggcagc tgtcccaagc aatgggtaat    1260
gatgatggca aaagggtgt ttggggaac agctgcagac ctgctgctct atgctcaccc     1320 ccgcccatt ctgggccaat gtgatttat ttatttgctc ccttggatac tgcaccttgg     1380
gtcccacttt ctccaggatg ccaactgcac tagctgtgtg cgaatgacgt atcttgtgca    1440
ttttaacttt tttccttaa tataaatatt ctggttttgt attttgtat attttaatct      1500 aaggccctca tttcctgcac tgtgttctca ggtacatgag caatctcagg atagccagc    1560 agcagctcca ggtctgcgca gcaggaatta ctttttgttg ttttgccac cgtggagagc     1620 aactatttgg agtgcacagc ctattgaact acctcattt tgccaataag agctggcttt    1680
tctgccatag tgtcctcttg aaacccctc tgccttgaaa atgttttatg ggagactagg    1740
ttttaactgg gtgcccccat gacttgattg ccttctactg gaagattggg aattagtcta    1800
aacaggaaat ggtggtacac agaggctagg agaggctggg cccggtgaaa aggccagaga    1860
gcaagccaag attaggtgag ggttgtctaa tcctatggca caggacgtgc tttacatctc    1920
cagatctgtt cttcaccaga ttaggttagg cctaccatgt gccacagggt gtgtgtgtgt    1980
ttgtaaaact agagttgcta aggataagtt taaagaccaa taccctgta cttaatcctg     2040 tgctgtcgag ggatggatat atgaagtaag gtgagatcct taaccttca aaattttcgg     2100 gttccaggga gacacacaag cgagggtttt gtggtgcctg gagcctgtgt cctgccctgc    2160
```

```
tacagtagtg attaatagtg tcatggtagc taaaggagaa aaaggggggtt tcgtttacac    2220 gctgtgagat caccgcaaac ctaccttact gtgttaaaac gggacaaatg caatagaacg    2280
cattgggtgg tgtgtgtctg atcctgggtt cttgtctccc ctaaatgctg ccccccaagt    2340
tactgtattt gtctgggctt tgtaggactt cactacgttg attgctaggt ggcctagttt    2400
gtgtaaatat aatgtattgg tcttctccg tgttctttgg gggttttgtt tacaaacttc     2460 ttttgtatt gagagaaaaa tagccaaagc atctttgaca gaaggttctg caccaggcaa     2520
aaagatctga acattagtt tggggggccc tcttcttaaa gtggggatct tgaaccatcc     2580
tttcttttgt attccccttc ccctattacc tattagacca gatcttctgt cctaaaaact    2640
tgtcttctac cctgccctct tttctgttca cccccaaaag aaaacttaca cacccacaca    2700
catacacatt tcatgcttgg agtgtctcca caactcttaa atgatgtatg caaaaatact    2760
gaagctagga aaaccctcca tcccttgttc ccaacctcct aagtcaagac cattaccatt    2820 tcttctttc ttttttttt ttttttaaaa tggagtctca ctgtgtcacc caggctggag     2880
tgcagtggca tgatcggctc actgcagcct ctgcctcttg ggttcaagtg attctcctgc    2940
ctcagcctcc tgagtagctg ggatttcagg caccgccac actcagctaa ttttgtatt     3000 tttagtagag acggggtttc accatgttgt ccaggctggt ctggaactcc tgacctcagg    3060
tgatctgccc accttggctt cccaaagtgc tgggattaca ggcatgagcc accatgctgg    3120
gccaaccatt tcttggtgta ttcatgccaa acacttaaga cactgctgta gcccaggcgc    3180
ggtggctcac acctgtaatc ccagcacttt ggaaggctga ggcgggcgga tcacaaggtc    3240
acgagttcaa aactatcctg gccaacacag tgaaaccccg tctctactaa aatacaaaaa    3300
aattagccgg gtgtggtggt gcatgccttt agtcctagct attcaggagg ctgaggcagg    3360
ggaatcgctt gaacccgaga ggcagaggtt gcagtgagct gagatcgcac cactgcactc    3420
cagcctggtt acagagcaag actctgtctc aaacaaaaca aaacaaaaca aaaacacact    3480
actgtatttt ggatggatca aacctcctta atttttaattt ctaatcctaa agtaaagaga   3540
tgcaattggg ggccttccat gtagaaagtg gggtcaggag gccaagaaag ggaatatgaa    3600
tgtatatcca agtcactcag gaacttttat gcaggtgcta gaaactttat gtcaaagtgg    3660
ccacaagatt gtttaatagg agacgaacga atgtaactcc atgtttactg ctaaaaacca    3720
aagctttgtg taaaatcttg aatttatggg gcgggagggt aggaaagcct gtacctgtct    3780 gttttttttcc tgatcctttt ccctcattcc tgaactgcag gagactgagc ccctttgggc   3840
tttggtgacc ccatcactgg ggtgtgttta tttgatggtt gattttgctg tactgggtac    3900
ttcctttccc atttctctaat catttttaa cacaagctga ctcttccctt cccttctcct    3960
ttccctggga aaatacaatg aataaataaa gacttattgg tacgcaaact gtca          4014
```

<210> SEQ ID NO 9
<211> LENGTH: 360
<212> TYPE: PRT
<213> ORGANISM: Homo sapiens

<400> SEQUENCE: 9

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
 50                  55                  60
Pro Pro Tyr Glu Phe Cys Gly Met Ala Tyr Cys Gly Pro Gln Val
 65                  70                  75                  80
Gly Val Gly Leu Val Pro Gln Gly Gly Leu Glu Thr Ser Gln Pro Glu
                 85                  90                  95
Gly Glu Ala Gly Val Gly Val Glu Ser Asn Ser Asp Gly Ala Ser Pro
             100                 105                 110
Glu Pro Cys Thr Val Thr Pro Gly Ala Val Lys Leu Glu Lys Glu Lys
             115                 120                 125
Leu Glu Gln Asn Pro Glu Glu Ser Gln Asp Ile Lys Ala Leu Gln Lys
             130                 135                 140
Glu Leu Glu Gln Phe Ala Lys Leu Leu Lys Gln Lys Arg Ile Thr Leu
145                 150                 155                 160
Gly Tyr Thr Gln Ala Asp Val Gly Leu Thr Leu Gly Val Leu Phe Gly
                 165                 170                 175
Lys Val Phe Ser Gln Thr Thr Ile Cys Arg Phe Glu Ala Leu Gln Leu
             180                 185                 190
Ser Phe Lys Asn Met Cys Lys Leu Arg Pro Leu Leu Gln Lys Trp Val
             195                 200                 205
Glu Glu Ala Asp Asn Asn Glu Asn Leu Gln Glu Ile Cys Lys Ala Glu
             210                 215                 220
Thr Leu Val Gln Ala Arg Lys Arg Lys Arg Thr Ser Ile Glu Asn Arg
225                 230                 235                 240
Val Arg Gly Asn Leu Glu Asn Leu Phe Leu Gln Cys Pro Lys Pro Thr
                 245                 250                 255
Leu Gln Gln Ile Ser His Ile Ala Gln Gln Leu Gly Leu Glu Lys Asp
             260                 265                 270
Val Val Arg Val Trp Phe Cys Asn Arg Arg Gln Lys Gly Lys Arg Ser
             275                 280                 285
Ser Ser Asp Tyr Ala Gln Arg Glu Asp Phe Glu Ala Ala Gly Ser Pro
             290                 295                 300
Phe Ser Gly Gly Pro Val Ser Phe Pro Leu Ala Pro Gly Pro His Phe
305                 310                 315                 320
Gly Thr Pro Gly Tyr Gly Ser Pro His Phe Thr Ala Leu Tyr Ser Ser
                 325                 330                 335
Val Pro Phe Pro Glu Gly Glu Ala Phe Pro Pro Val Ser Val Thr Thr
             340                 345                 350
Leu Gly Ser Pro Met His Ser Asn
             355                 360

<210> SEQ ID NO 10
<211> LENGTH: 1411
<212> TYPE: DNA
<213> ORGANISM: Homo sapiens

<400> SEQUENCE: 10
ccttcgcaag ccctcatttc accaggcccc cggcttgggg cgccttcctt ccccatggcg    60
ggacacctgg cttcggattt cgccttctcg ccccctccag gtggtggagg tgatgggcca   120
ggggggccgg agccgggctg ggttgatcct cggacctggc taagcttcca aggccctcct   180
ggagggccag gaatcgggcc gggggttggg ccaggctctg aggtgtgggg gattccccca   240
tgccccccgc cgtatgagtt ctgtgggggg atggcgtact gtgggcccca ggttggagtg   300
gggctagtgc cccaaggcgg cttggagacc tctcagcctg agggcgaagc aggagtcggg   360

```
gtggagagca actccgatgg ggcctccccg agccctgca ccgtcacccc tggtgccgtg      420
aagctggaga aggagaagct ggagcaaaac ccggaggagt cccaggacat caaagctctg      480
cagaaagaac tcgagcaatt tgccaagctc ctgaagcaga gaggatcac cctgggatat       540 acacaggccg atgtggggct caccctgggg gttctatttg gaaggtatt cagccaaacg       600 accatctgcc gctttgaggc tctgcagctt agcttcaaga acatgtgtaa gctgcggccc      660
ttgctgcaga agtgggtgga ggaagctgac aacaatgaaa atcttcagga gatatgcaaa      720
gcagaaaccc tcgtgcaggc ccgaaagaga aagcgaacca gtatcgagaa ccgagtgaga      780
ggcaacctgg agaatttgtt cctgcagtgc ccgaaaccca cactgcagca gatcagccac      840
atcgcccagc agcttgggct cgagaaggat gtggtccgag tgtggttctg taaccggcgc      900
cagaagggca agcgatcaag cagcgactat gcacaacgag aggattttga ggctgctggg      960
tctcctttct caggggggacc agtgtccttt cctctggccc cagggcccca ttttggtacc     1020
ccaggctatg ggagccctca cttcactgca ctgtactcct cggtcccttt ccctgagggg     1080
gaagcctttc ccctgtctc cgtcaccact ctgggctctc ccatgcattc aaactgaggt      1140
gcctgcccct ctaggaatgg gggacagggg gaggggagga gctagggaaa gaaaacctgg    1200
agtttgtgcc agggttttg ggattaagtt cttcattcac taaggaagga attgggaaca      1260
caaagggtgg gggcagggga gtttggggca actggttgga gggaaggtga agttcaatga    1320
tgctcttgat tttaatccca catcatgtat cacttttttc ttaaataaag aagcctggga    1380
cacagtagat agacacactt aaaaaaaaaa a                                    1411
```

```
<210> SEQ ID NO 11
<211> LENGTH: 317
<212> TYPE: PRT
<213> ORGANISM: Homo sapiens

<400> SEQUENCE: 11

Met Tyr Asn Met Met Glu Thr Glu Leu Lys Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
```

|     | 180 |     |     |     | 185 |     |     |     | 190 |     |     |
| --- | --- | --- | --- | --- | --- | --- | --- | --- | --- | --- | --- |

Gln Met Gln Pro Met His Arg Tyr Asp Val Ser Ala Leu Gln Tyr Asn
     195                             200                         205

Ser Met Thr Ser Ser Gln Thr Tyr Met Asn Gly Ser Pro Thr Tyr Ser
210                           215                         220

Met Ser Tyr Ser Gln Gln Gly Thr Pro Gly Met Ala Leu Gly Ser Met
225                   230                     235                  240

Gly Ser Val Val Lys Ser Glu Ala Ser Ser Pro Pro Val Val Thr
                 245                    250                 255

Ser Ser Ser His Ser Arg Ala Pro Cys Gln Ala Gly Asp Leu Arg Asp
          260                   265                    270

Met Ile Ser Met Tyr Leu Pro Gly Ala Glu Val Pro Glu Pro Ala Ala
     275                       280                    285

Pro Ser Arg Leu His Met Ser Gln His Tyr Gln Ser Gly Pro Val Pro
          290                   295                    300

Gly Thr Ala Ile Asn Gly Thr Leu Pro Leu Ser His Met
305                  310                    315

<210> SEQ ID NO 12
<211> LENGTH: 2520
<212> TYPE: DNA
<213> ORGANISM: Homo sapiens

<400> SEQUENCE: 12

```
ggatggttgt ctattaactt gttcaaaaaa gtatcaggag ttgtcaaggc agagaagaga      60
gtgtttgcaa aggggggaaa gtagtttgct gcctctttaa gactaggact gagagaaaga     120
agaggagaga gaaagaaagg gagagaagtt tgagccccag gcttaagcct ttccaaaaaa     180
taataataac aatcatcggc ggcgcagga tcggccagag gaggagggaa gcgcttttt      240
tgatcctgat tccagtttgc ctctctcttt ttttccccca aattattctt cgcctgattt     300
tcctcgcgga gccctgcgct cccgacaccc ccgcccgcct cccctcctcc tctcccccg      360
cccgcgggcc cccaaaagtc ccggccgggc cgagggtcgg cggccgccgg cgggccgggc     420
ccgcgcacag cgcccgcatg tacaacatga tggagacgga gctgaagccg ccgggcccgc     480
agcaaacttc ggggggcggc ggcggcaact ccaccgcggc ggcggccggc ggcaaccaga     540
aaaacagccc ggaccgcgtc aagcggccca tgaatgcctt catggtgtgg tcccgcgggc     600
agcggcgcaa gatggcccag gagaacccca agatgcacaa ctcggagatc agcaagcgcc     660
tgggcgccga gtggaaactt ttgtcggaga cggagaagcg gccgttcatc gacgaggcta     720
gcggctgcg agcgctgcac atgaaggagc acccggatta taaataccgg ccccggcgga     780
aaaccaagac gctcatgaag aaggataagt acacgctgcc cggcgggctg ctggcccccg     840
gcggcaatag catggcgagc ggggtcgggg tgggcgccgg cctgggcgcg ggcgtgaacc     900
agcgcatgga cagttacgcg cacatgaacg gctggagcaa cggcagctac agcatgatgc     960
aggaccagct gggctacccg cagcacccgg gcctcaatgc gcacggcgca gcgcagatgc    1020
agcccatgca ccgctacgac gtgagcgccc tgcagtacaa ctccatgacc agctcgcaga    1080
cctacatgaa cggctcgccc acctacagca tgtcctactc gcagcagggc acccctggca    1140
tggctcttgg ctccatgggt tcggtggtca agtccgaggc cagctccagc cccctgtgg    1200
ttacctcttc ctcccactcc agggcgccct gccaggccgg gaccctcgg gacatgatca    1260
gcatgtatct ccccggcgcc gaggtgccgg aacccgccgc ccccagcaga cttcacatgt    1320
cccagcacta ccagagcggc ccggtgcccg gcacggccat taacggcaca ctgccctct    1380
```

```
cacacatgtg agggccggac agcgaactgg agggggggaga aatttttcaaa gaaaaacgag    1440 ggaaatggga ggggtgcaaa agaggagagt aagaaacagc atggagaaaa cccggtacgc    1500
tcaaaaagaa aaaggaaaaa aaaaaatccc atcacccaca gcaaatgaca gctgcaaaag    1560
agaacaccaa tcccatccac actcacgcaa aaaccgcgat gccgacaaga aaacttttat    1620
gagagagatc ctggacttct ttttgggggga ctattttttgt acagagaaaa cctggggagg    1680
gtggggaggg cggggggaatg gaccttgtat agatctggag gaaagaaagc tacgaaaaac    1740
tttttaaaag ttctagtggt acggtaggag ctttgcagga agtttgcaaa agtctttacc    1800
aataatattt agagctagtc tccaagcgac gaaaaaaatg ttttaatatt tgcaagcaac    1860
ttttgtacag tatttatcga gataaacatg gcaatcaaaa tgtccattgt ttataagctg    1920
agaatttgcc aatattttttc aaggagaggc ttcttgctga atttttgattc tgcagctgaa    1980 atttaggaca gttgcaaacg tgaaagaag aaaattattc aaatttggac attttaattg    2040
tttaaaaatt gtacaaaagg aaaaaattag aataagtact ggcgaaccat ctctgtggtc    2100
ttgtttaaaa agggcaaaag ttttagactg tactaaattt tataacttac tgttaaaagc    2160
aaaaatggcc atgcaggttg acaccgttgg taatttataa tagcttttgt tcgatcccaa    2220 cttttccattt tgttcagata aaaaaaacca tgaaattact gtgtttgaaa tattttctta    2280
tggtttgtaa tatttctgta aatttattgt gatatttttaa ggttttcccc cctttatttt    2340
ccgtagttgt attttaaaag attcggctct gtattatttg aatcagtctg ccgagaatcc    2400
atgtatatat ttgaactaat atcatcctta taacaggtac attttcaact taagttttta    2460
ctccattatg cacagtttga gataaataaa tttttgaaat atggacactg aaaaaaaaaa    2520
```

<210> SEQ ID NO 13
<211> LENGTH: 16
<212> TYPE: PRT
<213> ORGANISM: Drosophila melanogaster

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Arg Arg Arg Arg Arg Arg Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Arg Arg Arg Arg Arg Arg
1               5

METHODS FOR NUCLEAR REPROGRAMMING OF CELLS

The instant application contains a Sequence Listing which has been submitted in ASCII format via EFS-Web and is hereby incorporated by reference in its entirety. Said ASCII copy, created on Sep. 20, 2013, is named 0132-0004PR1_SL.txt and is 39,860 bytes in size.

FIELD OF THE INVENTION

The invention relates to stem cell reprograming methods.

BACKGROUND OF THE INVENTION

The transformation of differentiated cells to induced pluripotent stem cells (iPSCs) has revolutionized stem cell biology by providing a more tractable source of pluripotent cells for regenerative therapy. The derivation of iPSCs from numerous normal and diseased cell sources has enabled the generation of stem cells for eventual use in cell therapy and regenerative medicine.

Seminal studies by Yamanaka and colleagues revealed that ectopic expression of certain transcriptional factors could induce pluripotency in somatic cells. These induced pluripotent stem cells self-renew and differentiate into a wide variety of cell types, making them an appealing option for disease- and regenerative medicine therapies. They have been used to successfully model human disease and have great potential for use in drug screening and cell therapy. Furthermore, iPSCs generated from diseased cells can serve as useful tools for studying disease mechanisms and potential therapies. However, much remains to be understood about the underlying mechanisms of reprogramming of somatic cells to iPSCs, and there is concern regarding potential clinical applications in the absence of mechanistic insights.

The original set of factors (RFs) for reprogramming to pluripotency include Oct3/4, Sox2, c-Myc, Klf4, Lin28, and Nanog. Oct3/4 and Sox2 are transcription factors that maintain pluripotency in embryonic stem (ES) cells while Klf4 and c-Myc are transcription factors thought to boost iPSC generation efficiency. The transcription factor c-Myc is believed to modify chromatin structure to allow Oct3/4 and Sox2 to more efficiently access genes necessary for reprogramming while Klf4 enhances the activation of certain genes by Oct3/4 and Sox2. Nanog, like Oct3/4 and Sox2, is a transcription factor that maintains pluripotency in ES cells while Lin28 is an mRNA-binding protein thought to influence the translation or stability of specific mRNAs during differentiation. It has also been shown that retroviral expression of Oct3/4 and Sox2, together with co-administration of valproic acid, a chromatin destabilizer and histone deacetylase inhibitor, is sufficient to reprogram fibroblasts into iPSCs.

Several classes of vectors have been shown to induce pluripotency when overexpressing the requisite gene combinations. The earliest vectors relied on DNA-integrating retroviruses and transposons for nuclear reprogramming. While effective, they inherently raise concerns about potential tumorigenicity either by insertional mutagenesis or re-expression of oncogenic reprogramming factors. While Cre-LoxP site gene delivery or PiggyBac transposon approaches have been used to excise foreign DNA from the host genome following gene delivery, neither strategy eliminates the risk of mutagenesis because they leave a small insert of residual foreign DNA.

As an alternative to genetic modification, mRNA, episomal DNA plasmids, and cell permeant proteins (CPP) have been shown to be effective for reprogramming factors.

These non-integrating vectors, however functional, often result in reduced reprogramming efficiencies either as a result of their specific mechanism of action or because of the cumbersome nature of their practice. Because, non-integrating and/or small-molecule based approaches for iPSC generation or transdifferentiation to a different somatic cell type are clinically relevant vectors, it becomes important to increase the robustness, efficiency, and ease of use of such methods. The present invention addresses these issues.

SUMMARY OF THE INVENTION

One aspect of the invention relates to a method of nuclear reprogramming of a mammalian somatic cell, the method comprising: contacting a population of mammalian somatic cells with (a) an effective dose of a damage-associated molecular pattern (DAMP) molecules; and (b) a cocktail of reprogramming factors; for a period of time sufficient to reprogram the mammalian somatic cells to desired cell type of interest.

In one embodiment of this aspect of the invention, the DAMP is an aluminum composition. In another embodiment, the aluminum composition and cocktail of non-integrating reprogramming factors are provided simultaneously. In another embodiment, the aluminum composition and cocktail of non-integrating reprogramming factors are provided sequentially. In still a further embodiment, the aluminum composition is selected from the group consisting of aluminum hydroxide, aluminum phosphate and aluminum sulfate. In still another embodiment, the aluminum composition is aluminum hydroxide. In yet another embodiment, the aluminum hydroxide is present in a concentration of about or at least 40-80 micrograms/ml. In still a further embodiment, the effective dose of the aluminum hydroxide is at least or about 30-60 micrograms/ml. In yet another embodiment, the aluminum composition is aluminum phosphate. In still another embodiment, the aluminum composition is aluminum sulfate.

In a further embodiment, the mammalian somatic cells are human cells. In still a further embodiment, the cocktail of reprogramming factors comprises use of Oct4, Sox2, Lin28, and Nanog, and the cells are reprogrammed to pluripotency. In still another embodiment, the cocktail of reprogramming factors comprises the use of Oct4, Sox2, c-Myc, and Klf4, and the cells are reprogrammed to pluripotency. In still another embodiment, the somatic cell type is peripheral blood mononuclear cell (PBMC), cord blood mononuclear cells, or fibroblasts. In yet a further embodiment, the reprogramming factors are provided as cell permeant proteins. In a further embodiment, the reprogramming factors are provided as nucleic acids encoding reprogramming proteins. In yet another embodiment, the desired cell type of interest is an induced pluripotent stem (iPS) cell.

Another aspect of the invention involves a method of nuclear reprogramming wherein the nuclear reprogramming efficiency is greater than if the method was carried out without the aluminum composition. In one embodiment of this aspect of the invention, the nuclear reprogramming efficiency is about 1 to about 5 fold greater with respect to the expression of at least one key pluripotency marker. In another embodiment, the nuclear reprogramming efficiency is about 1 to about 5 fold greater with respect to the amount of desired cell type of interest produced.

Another aspect of the invention relates to a population of induced pluripotent stem cells produced by any of the methods of the disclosure. In one embodiment, the induced pluripotent stem cells are human cells.

Another aspect of the invention relates to a kit for practicing the methods of the invention. In one embodiment the kit comprises reprogramming factors and an aluminum composition. In another embodiment, the kit further comprises somatic cells. Yet a further aspect relates to a therapeutic composition comprising a DAMP composition, such as an aluminum composition, and one or more reprograming factors and/or nucleic acids encoding the same and/or small molecules, for administration in vivo, for therapeutic modulation of cell and/or tissue phenotype. Another aspect relates to methods of treating a patient in need thereof by administering to the patient a therapeutically effective amount of the therapeutic compositions of the disclosure.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

Figure 1:
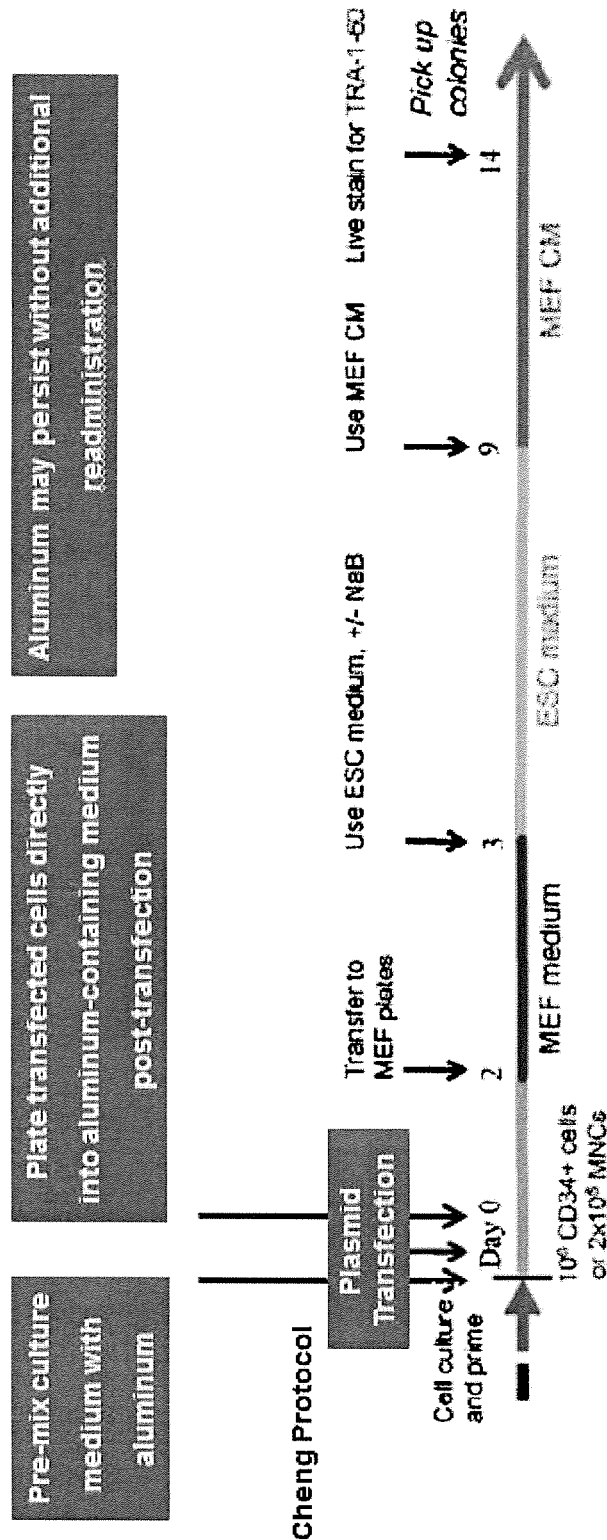
FIG. 1 shows an image of the process of obtaining iPSCs using methods described herein.
Figure 2:
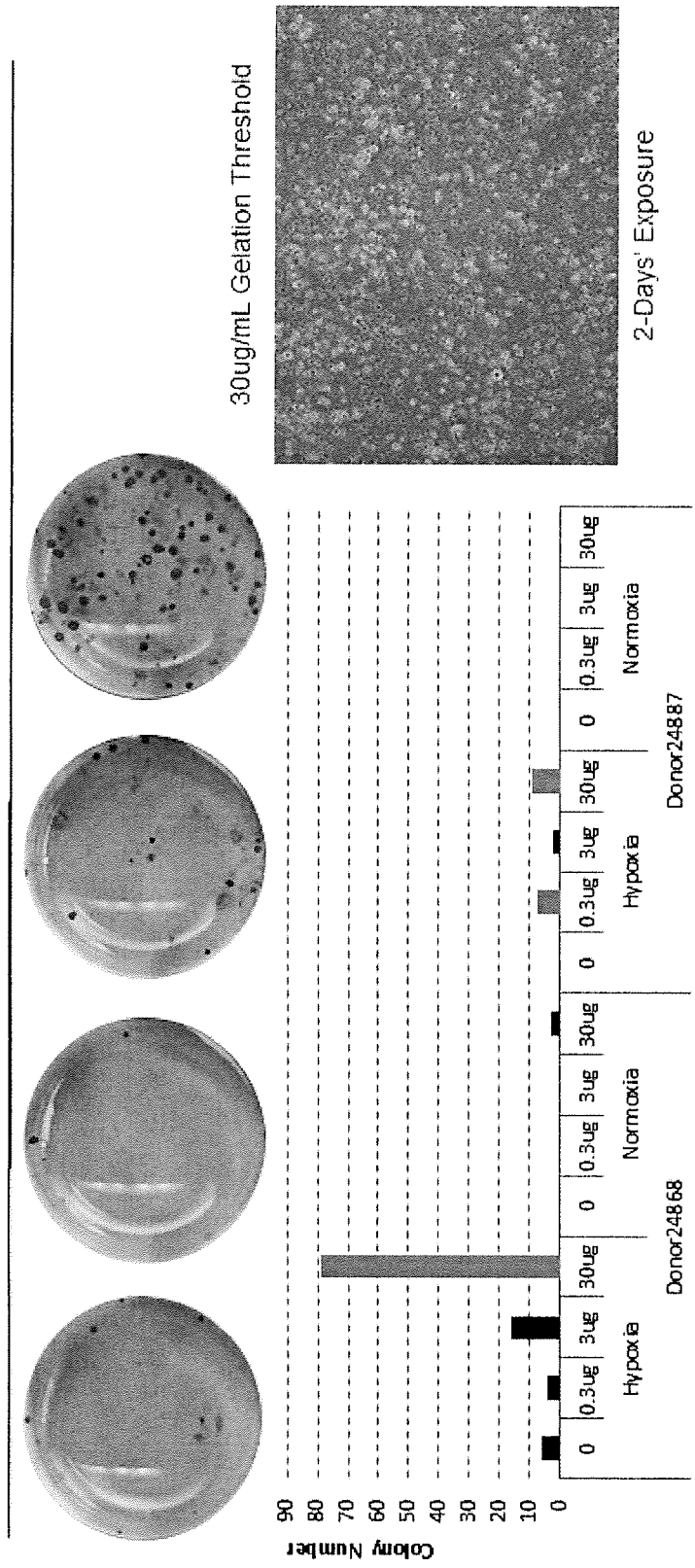
FIGS. 2, 3, 4 and 5 illustrate experimental results of using varying concentrations of aluminum hydroxide to obtain iPSCs from various donors under hypoxic and normoxic conditions using the methods disclosed herein.
Figure 3:
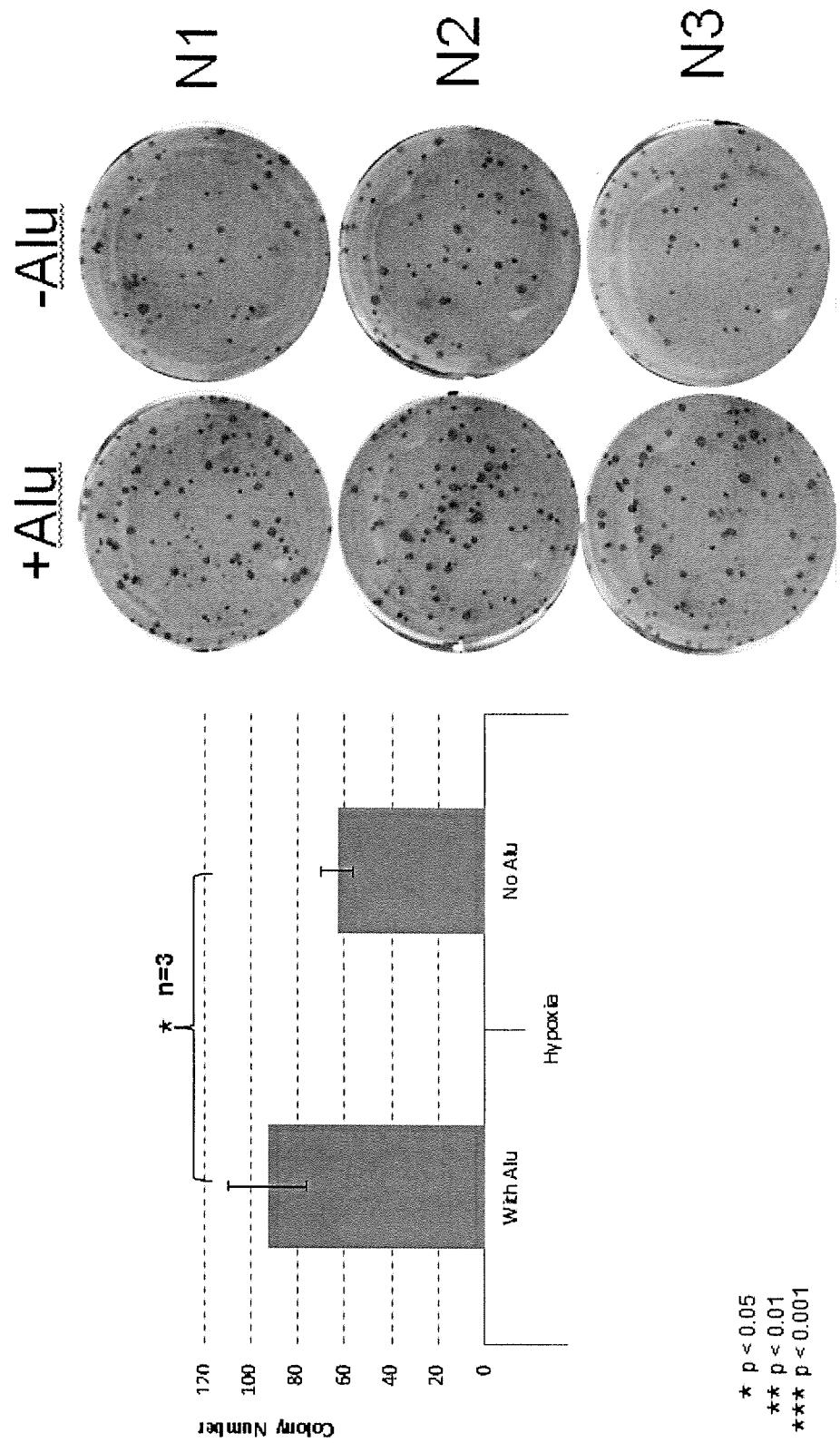
Figure 4:
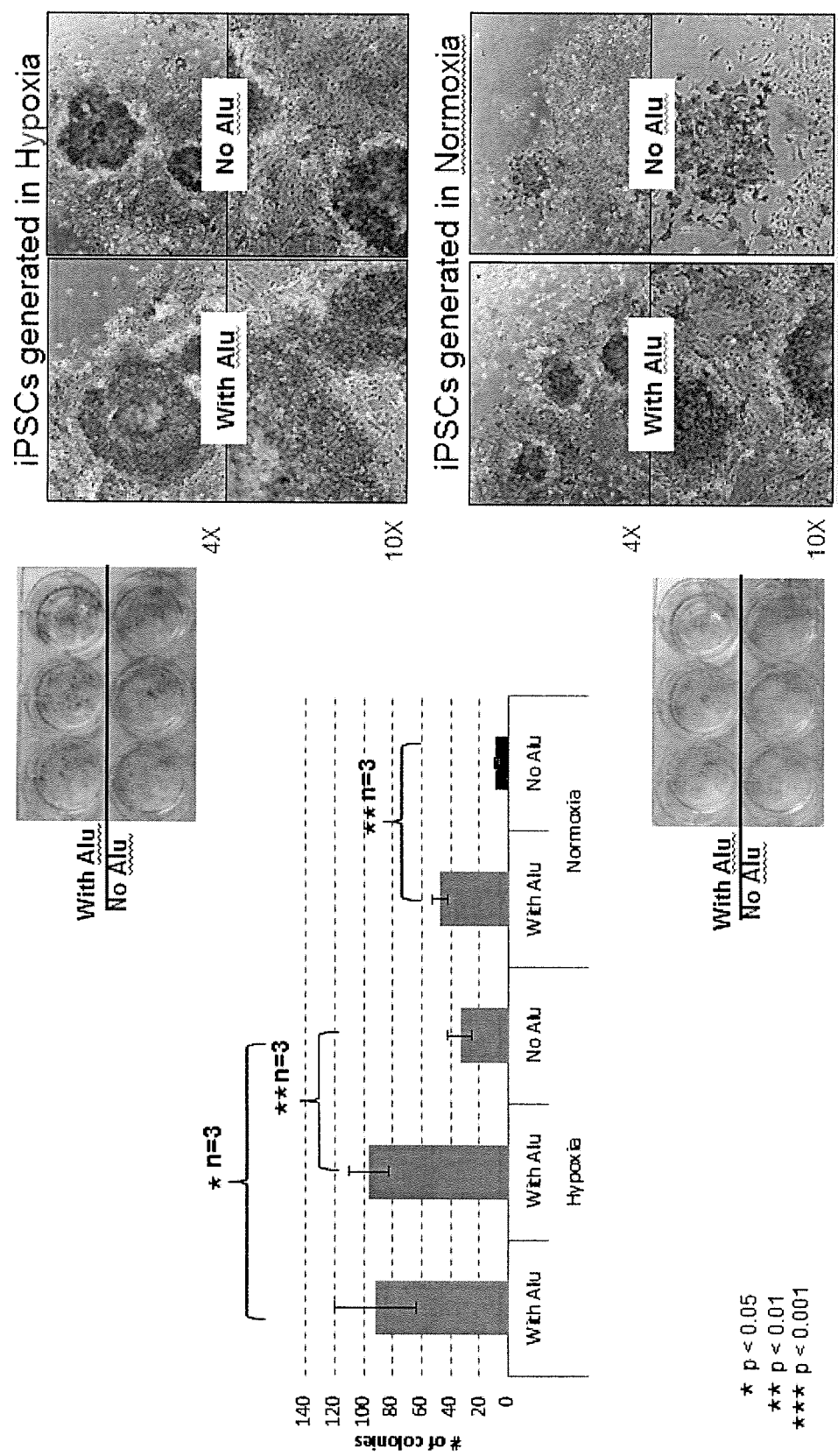
Figure 5:
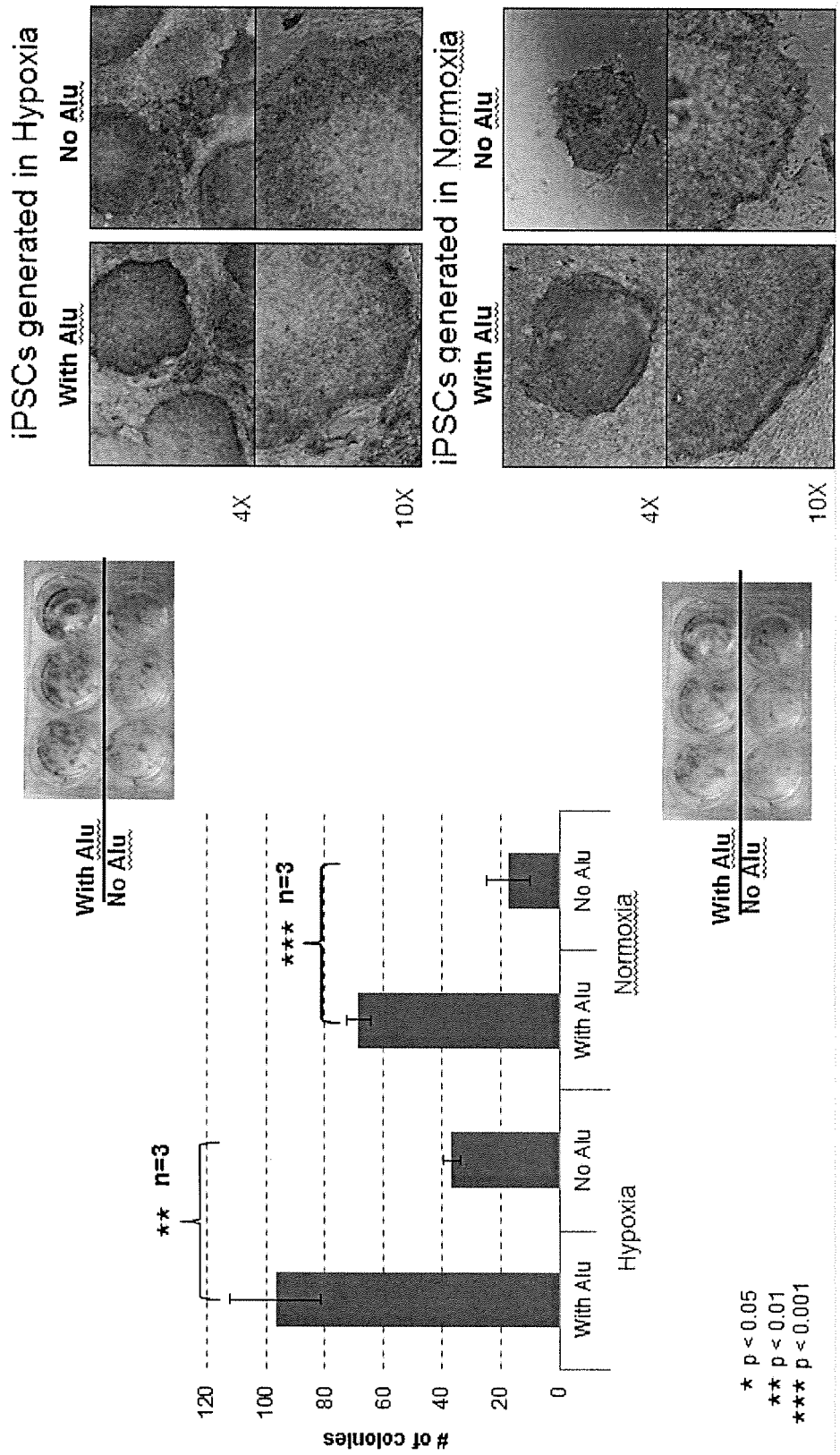

Described herein are methods for enhancing the nuclear reprogramming of somatic cells to become induced pluripotent stem cells. In particular, the methods disclosed herein involve the use of damage-associated molecular pattern molecules (DAMPs). In certain embodiments the DAMPs are aluminum compositions such as aluminum hydroxide. Such DAMPs have unexpectedly and surprisingly been found to enhance the nuclear reprogramming efficiency of the reprogramming factors commonly used to induce somatic cells to become induced pluripotent stem cells. Accordingly, this disclosure describes methods of nuclear reprogramming as well as cells obtained from such methods along with therapeutic methods for using such cells for the treatment of diseases amendable to treatment by stem cell therapy as well as kits for such uses.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

"Totipotency" is referred to herein as the ability of a single cell to divide and/or differentiate to produce all the differentiated cells in an organism, including extra-embryonic tissues. Totipotent cells include spores and zygotes. In some organisms, cells can dedifferentiate and regain totipotency.

"Pluripotency" is referred to herein as the potential to differentiate into any of the three germ layers: endoderm (interior stomach lining, gastrointestinal tract, the lungs), mesoderm (muscle, bone, blood, urogenital), or ectoderm (epidermal tissues and nervous system).

"Pluripotent stem cells" include natural pluripotent stem cells and induced pluripotent stem cells. They can give rise to any fetal or adult cell type. However, alone they generally cannot develop into a fetal or adult organism because they lack the potential to contribute to extra-embryonic tissue, such as the placenta.

"Induced pluripotent stem cells" or ("iPSCs") are similar to natural pluripotent stem cells, such as embryonic stem (ES) cells, in many aspects, such as the expression of certain stem cell genes and/or proteins, chromatin methylation patterns, doubling time, embryoid body formation, teratoma formation, viable chimera formation, and potency and differentiability. Induced pluripotent cells may be derived from for example, adult stomach, liver, skin cells and blood cells. iPSCs may be derived by transfection of certain stem cell-associated genes into non-pluripotent cells, such as adult fibroblasts. In certain embodiments, transfection may be achieved through viral vectors, such as retroviruses, for example, and non-viral or episomal vectors. Transfected genes can include, but are not limited to, master transcriptional factors Oct-3/4 (Pou5f1), Klf4, c-myc, Sox2, Oct-4, Nanog and Lin28 transgenes). Sub-populations of transfected cells may begin to become morphologically and biochemically similar to pluripotent stem cells, and can be isolated through morphological selection, doubling time, or through a reporter gene and antibiotic selection.

"Key pluripotency markers" known by one of ordinary skill in the art include but are not limited to the gene and/or protein expression of alkaline phosphatase, SSEA3, SSEA4, Sox2, Oct3/4, Nanog, TRA160, TRA181, TDGF 1, Dnmt3b, FoxD3, Cyp26a1, TERT, and zfp42.

"Multipotency" is referred to herein as multipotent progenitor cells which have the potential to give rise to multiple cell types, but a number of lineages more limited than a pluripotent stem cell. For example, a multipotent stem cell is a hematopoietic cell that can develop into several types of blood cells, but cannot develop into brain cells or other types of cells.

"Reprogramming factors," as used herein, refers to one or a cocktail of biologically active polypeptides (or nucleic acids, e.g., DNA or RNA, encoding them) or small molecules that act on a cell to alter transcription, and which upon expression, reprogram a somatic cell to a different cell type, or to multipotency or to pluripotency. In some embodiments, the reprogramming factors may be non-integrating, i.e., provided to the recipient somatic cell in a form that does not result in integration of exogenous DNA into the genome of the recipient cell.

In some embodiments the reprogramming factor is a transcription factor, including without limitation, Oct3/4; Sox2; Klf4; c-Myc; and Nanog. Also of interest as a reprogramming factor is Lin28, which is an mRNA-binding protein thought to influence the translation or stability of specific mRNAs during differentiation.

Reprogramming factors of interest also include factors useful in transdifferentiation, where a somatic cell is reprogrammed to a different somatic cell. For the purpose of transdifferentiation of one somatic cell to another, substantially different, somatic cell type, a different set of reprogramming factors finds use. For example, to transdifferentiate a fibroblast to a cardiomyocyte, one might use cell permeant peptides Gata4, Mef2c and Tbx5 (Leda et al., Cell, Volume 142, Issue 3, 375-386, 6 Aug. 2010, herein specifically incorporated by reference.)

The reprogramming factors may be provided as compositions of isolated polypeptides, i.e. in a cell-free form, which are biologically active or as a nucleic acids (e.g., DNA, RNA) encoding the same. Biological activity may be determined by specific DNA binding assays; or by determining the effectiveness of the factor in altering cellular transcription. A composition of the invention may provide one or more biologically active reprogramming factors. The composition may comprise at least about 50 µg/ml soluble reprogramming factor, at least about 100 µg/ml; at least about 150 at least about 200 µg/ml, at least about 250 µg/ml, at least about 300 µg/ml, or more.

A Klf4 polypeptide is a polypeptide comprising the amino acid sequence that is at least 70% identical to the amino acid sequence of human Klf4, i.e., Kruppel-Like Factor 4 the sequence of which may be found at GenBank Accession Nos. NP_004226 (SEQ ID NO: 1) and NM_004235 (SEQ ID NO: 2). Klf4 polypeptides, e.g. those that are at least 70%, 75%, 80%, 85%, 90%, 91%, 92%, 95%, 97%, 99%, or 100% identical to the sequence provided in GenBank Accession No. NM_004235 (SEQ ID NO: 2), and the nucleic acids that encode them find use as a reprogramming factor in the present invention.

A c-Myc polypeptide is a polypeptide comprising an amino acid sequence that is at least 70% identical to the amino acid sequence of human c-Myc, i.e., myelocytomatosis viral oncogene homolog, the sequence of which may be found at GenBank Accession Nos. NP_002458 (SEQ ID NO: 3) and NM_002467 (SEQ ID NO: 4). c-Myc polypeptides, e.g. those that are at least 70%, 75%, 80%, 85%, 90%, 91%, 92%, 95%, 97%, 99%, or 100% identical to the sequence provided in GenBank Accession No. NM_002467 (SEQ ID NO: 4), and the nucleic acids that encode them find use as a reprogramming factor in the present invention.

A Nanog polypeptide is a polypeptide comprising an amino acid sequence that is at least 70% identical to the amino acid sequence of human Nanog, i.e., Nanog homeobox, the sequence of which may be found at GenBank Accession Nos. NP_079141 (SEQ ID NO: 5) and NM_024865 (SEQ ID NO: 6). Nanog polypeptides, e.g. those that are at least 70%, 75%, 80%, 85%, 90%, 91%, 92%, 95%, 97%, 99%, or 100% identical to the sequence provided in GenBank Accession No. NM_024865 (SEQ ID NO: 6), and the nucleic acids that encode them find use as a reprogramming factor in the present invention.

A Lin-28 polypeptide is a polypeptide comprising an amino acid sequence that is at least 70% identical to the amino acid sequence of human Lin-28, i.e., Lin-28 homolog of C. elegans, the sequence of which may be found at GenBank Accession Nos. NP_078950 (SEQ ID NO: 7) and NM_024674 (SEQ ID NO: 8). Lin-28 polypeptides, e.g. those that are at least 70%, 75%, 80%, 85%, 90%, 91%, 92%, 95%, 97%, 99%, or 100% identical to the sequence provided in GenBank Accession No. NM_024674 (SEQ ID NO: 8), and the nucleic acids that encode them find use as a reprogramming factor in the present invention.

An Oct3/4 polypeptide is a polypeptide comprising an amino acid sequence that is at least 70% identical to the amino acid sequence of human Oct3/4, also known as Homo sapiens POU class 5 homeobox 1 (POU5F1) the sequence of which may be found at GenBank Accession Nos. NP_002692 (SEQ ID NO: 9) and NMP_002701 (SEQ ID NO: 10). Oct3/4 polypeptides, e.g. those that are at least 70%, 75%, 80%, 85%, 90%, 91%, 92%, 95%, 97%, 99%, or 100% identical to the sequence provided in GenBank Accession No. NM_002701 (SEQ ID NO: 10), and the nucleic acids that encode them find use as a reprogramming factor in the present invention.

A Sox2 polypeptide is a polypeptide comprising the amino acid sequence at least 70% identical to the amino acid sequence of human Sox2, i.e., sex-determining region Y-box 2 protein, the sequence of which may be found at GenBank Accession Nos. NP_003097 (SEQ ID NO: 11) and NM_003106 (SEQ ID NO: 12). Sox2 polypeptides, e.g. those that are at least 70%, 75%, 80%, 85%, 90%, 91%, 92%, 95%, 97%, 99%, or 100% identical to the sequence provided in GenBank Accession No. NM_003106 (SEQ ID NO: 12), and the nucleic acids that encode them find use as a reprogramming factor in the present invention.

Small molecules, including without limitation valproic acid, hydroxamic acid, trichostatin A, suberoylanilide hydroxamic acid, BIX-01294 and BayK8644 have been described as useful in reprogramming cells (see Shi et al. (2008) Cell Stem Cell 6; 3(5):568-574 and Huangfu et al. (2008) Nature Biotechnology 26:795-797, each herein specifically incorporated by reference).

"Damage-associated molecular pattern molecules" (DAMPs) also known as danger-associated molecular pattern molecules, as used herein are molecules that can initiate and perpetuate immune responses in a noninfectious inflammatory response. In contrast, Pathogen-associated molecular pattern molecules (PAMPs) initiate and perpetuate the infectious pathogen inflammatory response. DAMPs may be nuclear or cytosolic proteins. When released outside the cell or exposed on the surface of the cell following tissue injury, they may move from a reducing to an oxidizing milieu, which can result in their denaturation. Following necrosis, tumor DNA is released outside the nucleus, and outside the cell, which may become a DAMP. Examples of DAMPs can include but are not limited to HMGB1, DNA, RNA, S100 molecules, purine metabolites, uric acid, nanoparticles, asbestos, aluminum compositions such as aluminum salts, beta-amyloid, silica, cholesterol crystals, hemozoin, calcium pyrophosphate dehydrate and the like. In certain embodiments, the presence of DAMPs is able to enhance the efficiency of reprograming as a result of exposure to the reprograming factors.

"Aluminum compositions" as used herein refers to molecules containing elemental aluminum, aluminum salts, aluminum ions and/or aluminum covalently or ionically bonded to another element. In some embodiments, the term relates to aluminum salts, aluminum hydroxides, aluminum sulfates and aluminum phosphates.

"Aluminum" is a chemical element in the boron group with symbol Al and atomic number 13. It is a silvery white, soft, ductile metal. Aluminum is the third most abundant element (after oxygen and silicon), and the most abundant metal, in the Earth's crust. The majority of compounds, including all Al-containing minerals and all commercially significant aluminum compounds, feature aluminum in the oxidation state 3+. The coordination number of such compounds varies, but generally Al3+ is six-coordinate or tetracoordinate. Almost all compounds of aluminum (III) are colorless. Aluminum forms one stable oxide, known by its mineral name corundum. Sapphire and ruby are impure corundum contaminated with trace amounts of other metals. The two oxide-hydroxides, AlO(OH), are boehmite and diaspore. There are three trihydroxides: bayerite, gibbsite, and nordstrandite, which differ in their crystalline structure (polymorphs). Most are produced from ores by a variety of wet processes using acid and base. Heating the hydroxides leads to formation of corundum.

"Aluminum hydroxide" as referred to herein is $Al(OH)_3$, ATH, sometimes erroneously called hydrate of alumina, is found in nature as the mineral gibbsite (also known as hydrargillite) and its three, more rare polymorphs: bayerite, doyleite and nordstrandite. Freshly precipitated aluminum hydroxide forms gels, which is the basis for application of aluminum salts as flocculants in water purification. This gel crystallizes with time. Aluminum hydroxide gels can be dehydrated (e.g., using water-miscible non-aqueous solvents like ethanol) to form an amorphous aluminum hydroxide powder, which is readily soluble in acids. Aluminum hydroxide powder which has been heated to an elevated temperature under carefully controlled conditions is known as activated alumina and is used as a desiccant, an adsorbent, in gas purification, as a Claus catalyst support, water purification, and an adsorbent for the catalyst during the manufacture of polyethylene by the Sclairtech process. Gibbsite has a typical metal hydroxide structure with hydrogen bonds. It is built up of double layers of hydroxyl groups with aluminum ions occupying two-thirds of the octahedral holes between the two layers.

Aluminum hydroxide may be commercially manufactured by the Bayer process which involves dissolving bauxite in sodium hydroxide at temperatures up to 270° C. The remaining solids, which is a red mud, is separated and aluminum oxide is precipitated from the remaining solution. The aluminum oxide that is produced can be converted to aluminum hydroxide through reaction with water.

"Aluminum Phosphate" ($AlPO_4$) is a chemical compound whose anhydrous form is found in nature as the mineral berlinite. Many synthetic forms of anhydrous aluminum phosphate are also known. They have framework structures similar to zeolites and some are used as catalysts or molecular sieves. A hydrated form, $AlPO_4 \cdot 1.5H_2O$ is known. An aluminum phosphate gel is also commercially available. There are a large number of aluminum phosphate molecular sieves, generically known as 'ALPOs'. They share the same chemical composition of $AlPO_4$ and have framework structures with microporous cavities and the frameworks are made up of alternating $AlO_4$ and $PO_4$ tetrahedra. The denser cavity-less crystalline $AlPO_4$ mineral, berlinite shares the same alternating $AlO_4$ and $PO_4$ tetrahedra. The aluminophosphate framework structures vary one from another in the orientation of the $AlO_4$ tetrahedra and $PO_4$ tetrahedra to form different sized cavities and in this respect they are similar to the aluminosilicate zeolites which differ in having electrically charged frameworks. A typical preparation of an aluminophosphate involves the hydrothermal reaction of phosphoric acid and aluminum in the form of hydroxide, an aluminum salt such as aluminum nitrate salt or alkoxide under controlled pH in the presence of organic amines. These organic molecules act as templates, (now termed structure directing agents to direct the growth of the porous framework).

"Aluminum sulfate" is a chemical compound with the formula $Al_2(SO_4)_3$. It is soluble in water and is mainly used as a flocculating agent in the purification of drinking water. Aluminum sulfate is sometimes referred to as a type of alum. Alums are a class of related compounds typified by $AB(SO_4)_2 \cdot 12H_2O$. The anhydrous form occurs naturally as a rare mineral millosevichite, found e.g. in volcanic environments and on burning coal-mining waste dumps. Aluminum sulfate is rarely, if ever, encountered as the anhydrous salt. It forms a number of different hydrates, of which the hexadecahydrate $Al_2(SO_4)_3 \cdot 16H_2O$ and octadecahydrate $Al_2(SO_4)_3 \cdot 18H_2O$ are the most common. The heptadecahydrate, whose formula can be written as $[Al(H_2O)_6]_2(SO_4)_3 \cdot 5H_2O$, occurs naturally as the mineral alunogen.

The dose of a DAMP (e.g., an aluminum composition) that is effective in the methods of the invention is a dose that increases the efficiency of reprogramming of a cell or cell population, relative to the same method conducted in the absence of the DAMP. The term "reprogramming" as used herein means nuclear reprogramming of a somatic cell to a pluripotential cell (e.g., a fibroblast to an induced pluripotential cell) or nuclear reprogramming of a somatic cell to a substantially different somatic cell (e.g., a fibroblast to an endothelial cell), in vitro or in vivo. The latter process is also known as transdifferentiation.

In certain embodiments, the cells being reprogramed are exposed to a concentration of DAMP such as an aluminum composition, having a concentration of about or at least or exactly 1, 10, $10^2$ or $10^3$ times 1, 2, 3, 4, 5, 6, 7, 8, 9, 10, 11, 12, 13, 14, 15, 16, 17, 181, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nanograms, micrograms, milligrams or grams per ml of cell culture medium. In another embodiment, the cells are exposed to such a concentration for about or at least or exactly 1, 2, 3, 4, 5, 6, 7, 8, 9, 10, 11, 12, 13, 14, 15, 16, 17, 181, 19, 20, 21, 22, 23, 24 minutes, hours or days before, after or during exposure of the somatic cells to reprograming factors.

The term "efficiency of reprogramming" may be used to refer to the ability of cells to give rise to iPS cell colonies when contacted with reprogramming factors. Somatic cells that demonstrate an enhanced efficiency of reprogramming to pluripotentiality will demonstrate an enhanced ability to give rise to iPSCs when contacted with reprogramming factors relative to a control. The term "efficiency of reprogramming" may also refer to the ability of somatic cells to be reprogrammed to a substantially different somatic cell type, a process known as transdifferentiation. The efficiency of reprogramming with the methods of the invention vary with the particular combination of somatic cells, method of introducing reprogramming factors, and method of culture following induction of reprogramming.

In certain embodiments, the presence of a DAMP results in about or at least or exactly 1, 10, $10^2$ or $10^3$ times 1, 2, 3, 4, 5, 6, 7, 8, 9, 10, 11, 12, 13, 14, 15, 16, 17, 181, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentage increase in: 1) the expression level of one or more key pluripotency markers; or 2) the number of iPSCs formed, each in comparison to the same method for reprogramming but lacking the DAMP (i.e., a control).

Methods of Inducing Pluripotency In Vitro

A starting population of somatic cells is contacted with reprogramming factors, as defined above, in a combination and quantity sufficient to reprogram the cell to pluripotency prior to, concurrent with or following activation of the somatic cell with an effective dose of a DAMP. In one embodiment of the invention, the aluminum composition is aluminum hydroxide. Reprogramming factors may be provided to the somatic cells individually or as a single composition, that is, as a premixed composition, of reprogramming factors. In another embodiment, the starting population of somatic cells is peripheral blood mononuclear cells (PBMCs), cord blood mononuclear cells, or fibroblasts.

In some embodiments, the starting population of cells is contacted with an effective dose of a DAMP from a period of time from about 1 to about 18 days, e.g. from about 1 to about 5 days, and may be around 2 to 3 days.

The reprogramming factors may be added to the subject cells simultaneously or sequentially at different times, and may be added in combination with the DAMP. In some embodiments, a set of at least three purified reprogramming factors is added, e.g., an Oct3/4 polypeptide, a Sox2 polypeptide, and a Klf4, c-myc, nanog or lin28 polypeptide. In some embodiments, a set of four purified reprogramming factors is provided to the cells e.g., an Oct3/4 polypeptide, a Sox2 polypeptide, a Klf4 polypeptide and a c-Myc polypeptide; or an Oct3/4 polypeptide, a Sox2 polypeptide, a lin28 polypeptide and a nanog polypeptide.

Methods for introducing the reprogramming factors to somatic cells include providing a cell with purified protein factors or nucleic acids encoding them. In some embodiments, a reprogramming factor will comprise the polypeptide sequences of the reprogramming factor fused to a polypeptide permeant domain. A number of permeant domains are known in the art and may be used in the nuclear acting, non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 13). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine (SEQ ID NO: 14), octa-arginine (SEQ ID NO: 15), and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. patent applications 20030220334; 20030083256; 20030032593; and 20030022831, herein specifically incorporated by reference for the teachings of translocation peptides and peptoids). The nona-arginine (R9) (SEQ ID NO: 14) sequence is one of the more efficient PTDs that have been characterized (Wender et al. 2000; Uemura et al. 2002).

In such embodiments, cells are incubated in the presence of a purified reprogramming factor for about 30 minutes to about 72 hours, e.g., 2 hours, 4 hours, 8 hours, 12 hours, 18 hours, 24 hours 36 hours, 48 hours, 60 hours, 72 hours, or any other period from about 30 minutes to about 72 hours. Typically, the reprogramming factors are provided to the subject cells four times, and the cells are allowed to incubate with the reprogramming factors for 48 hours, after which time the media is replaced with fresh media and the cells are cultured further (See, for example, Zhou et al. (2009) Cell Stem Cells 4(5); 381-384). The reprogramming factors may be provided to the subject cells for about one to about 4 weeks, e.g. from about two to about 3 weeks.

The dose of reprogramming factors will vary with the nature of the cells, the factors, the culture conditions, etc. In some embodiments the dose will be from about 1 nM to about 1 µM for each factor, more usually from about 10 nM to about 500 nM, or around about 100 to 200 nM. In some embodiments, the cells are initially exposed to an aluminum composition during exposure to the reprogramming actors for at least about 1 day, at least about 2 days, at least about 4 days, at least about 6 days or one week, and may be exposed for the entire reprogramming process, or less. The dose will depend on the specific DAMP, but may be from about 1 ng/ml to about 1 µg/ml, from about 10 ng/ml to about 500 ng/ml. Two 16-24 hour incubations with the recombination factors may follow each provision, after which the media is replaced with fresh media and the cells are cultured further.

In some embodiments, a vector that does not integrate into the somatic cell genome is used. Many vectors useful for transferring exogenous genes into target mammalian cells are available. The vectors may be maintained episomally, e.g. as plasmids, virus-derived vectors such cytomegalovirus, adenovirus, etc. Vectors used for providing reprogramming factors to the subject cells as nucleic acids will typically comprise suitable promoters for driving the expression, that is, transcriptional activation, of the reprogramming factor nucleic acids. This may include ubiquitously acting promoters, for example, the CMV-beta-actin promoter, or inducible promoters, such as promoters that are active in particular cell populations or that respond to the presence of drugs such as tetracycline. By transcriptional activation, it is intended that transcription will be increased above basal levels in the target cell by at least or about 2, 3, 4, 5, 6, 7, 8, 9, 10, 100 or 1000 fold.

Following introduction of reprogramming factors, the somatic cells may be maintained in a conventional culture medium comprising feeder layer cells, or may be cultured in the absence of feeder layers, i.e. lacking somatic cells other than those being induced to pluripotency. Feeder layer free cultures may utilize a protein coated surface, e.g. matrigel, etc. The somatic cells may also be maintained in suspension or attached to microcarriers.

iPSCs induced to become such by the methods of the invention may have an hESC-like morphology, growing as flat colonies with large nucleo-cytoplasmic ratios, defined borders and prominent nuclei. In addition, the iPSCs may express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPSCs are capable of forming teratomas. In addition, they are capable of forming or contributing to ectoderm, mesoderm, or endoderm tissues in a living organism.

Genes may be introduced into the somatic cells or the iPSCs derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The iPSCs produced by the above methods may be used for reconstituting or supplementing differentiating or differentiated cells in a recipient. The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

The induced cells, or cells differentiated from the induced cells, may be used as a therapy to treat disease (e.g., a genetic defect). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The iPSCs may be administered in any physiologically acceptable medium. They may be provided alone or with a suitable substrate or matrix, e.g. to support their growth and/or organization in the tissue to which they are being transplanted. Usually, at least $1 \times 10^5$ cells will be administered, preferably $1 \times 10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Kits may be provided, where the kit comprises an effective dose of a DAMP such as an aluminum composition. In some embodiments the aluminum composition is a aluminum hydroxide. The kit may further comprise one or more reprogramming factors, e.g. in the form of proteins fused to a permeant domain.

"Treating" or "treatment" is referred to herein as administration of a substance to a subject with the purpose to cure, alleviate, relieve, remedy, prevent, or ameliorate a disorder, symptoms of the disorder, a disease state secondary to the disorder, or predisposition toward the disorder. An "effective amount" is an amount of the substance that is capable of producing a medically desirable result as delineated herein in a treated subject. The medically desirable result may be objective (i.e., measurable by some test or marker) or subjective (i.e., subject gives an indication of or feels an effect).

"Disease amenable to treatment with stem cell therapy" as referred to herein means any procedures, conditions, disorders, ailments and/or illnesses which can be treated by the administration of stem cells such as iPSCs. Such diseases include but are not limited to bone marrow, skin, heart, and corneal transplantation, graft versus host disease, hepatic and renal failure, lung injury, rheumatoid arthritis, treatment of autoimmune diseases such as Crohn's disease, ulcerative colitis, multiple sclerosis, lupus and diabetes; prevention of allograft rejection, neurological disorders and cardiovascular medicine; as well as Acute lymphoblastic leukemia (ALL), Acute myeloid leukemia (AML), Burkitt's lymphoma, Chronic myeloid leukemia (CML), Juvenile myelomonocytic leukemia (JMML), Non-Hodgkin's lymphoma Hodgkin's lymphoma, Lymphomatoid granulomatosis, Myelodysplastic syndrome (MDS), Chronic myelomonocytic leukemia (CMML), Bone Marrow Failure Syndromes, Amegakaryocytic thrombocytopenia, Autoimmune neutropenia (severe), Congenital dyserythropoietic anemia, Cyclic neutropenia, Diamond-Blackfan anemia, Evan's syndrome, Fanconi anemia, Glanzmann's disease, Juvenile dermatomyositis, Kostmann's syndrome, Red cell aplasia, Schwachman syndrome, Severe aplastic anemia, Congenital sideroblastic anemia, Thrombocytopenia with absent radius (TAR syndrome), Dyskeratosis congenital, Blood Disorders, Sickle-cell anemia (hemoglobin SS), HbSC disease, Sickle βo Thalassemia, α-thalassemia major (hydrops fetalis), β-thalassemia major (Cooley's anemia), β-thalassemia intermedia, E-βo thalassemia, E-β+ thalassemia, Metabolic Disorders, Adrenoleukodystrophy Gaucher's disease (infantile), Metachromatic leukodystrophy, Krabbe disease (globoid cell leukodystrophy), Gunther disease, Hermansky-Pudlak syndrome, Hurler syndrome, Hurler-Scheie syndrome, Hunter syndrome, Sanfilippo syndrome, Maroteaux-Lamy syndrome, Mucolipidosis Type II, III, Alpha mannosidosis, Niemann Pick Syndrome, type A and B, Sandhoff Syndrome, Tay-Sachs Disease, Batten disease (inherited neuronal ceroid lipofuscinosis), Lesch-Nyhan disease, Immunodeficiencies, Ataxia telangiectasia, Chronic granulomatous disease, DiGeorge syndrome, IKK gamma deficiency, Immune dysregulation polyendocrineopathy, X-linked Mucolipidosis, Type II, Myelokathexis X-linked immunodeficiency, Severe combined immunodeficiency, Adenosine deaminase deficiency, Wiskott-Aldrich syndrome, X-linked agammaglobulinemia, X-linked lymphoproliferative disease, Omenn's syndrome, Reticular dysplasia, Thymic dysplasia, Leukocyte adhesion deficiency, Other Osteopetros is, Langerhans cell histiocytosis, Hemophagocytic lymphohistiocytosis, Acute & Chronic Kidney Disease, Alzheimer's disease, Anti-Aging, Arthritis, Asthma, Cardiac Stem Cell Therapy, Cerebral Infarction (Stroke), Cerebral Palsy (Stroke), Chronic Obstructive Pulmonary Disease (COPD), Congestive Heart Failure, Diabetes Mellitus (Type I & II), Fibromyalgia, Immune Deficiencies, Ischemic Heart Disease, Lupus, Multiple Sclerosis, Myocardial Infarction, Osteoarthritis, Osteoporosis, Parkinson's Disease, Peripheral Arterial Disease, Rheumatoid Arthritis, Stem Cell Therapy in Plastic Surgery, Traumatic Brain Injury and Neurological Diseases.

"Patient" as used herein refers to a mammalian subject diagnosed with or suspected of having or developing a disease amenable to stem cell therapy, e.g., cardiovascular disease. Exemplary patients may be humans, apes, dogs, pigs, cattle, cats, horses, goats, sheep, rodents and other mammalians that can benefit from stem cell therapies.

"Administering" is referred to herein as providing the iPSCs of the invention to a patient. By way of example and not limitation, composition administration, e.g., injection, may be performed by intravenous (i.v.) injection, subcutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device, e.g., a stent, loaded with cells. Preferably, the compositions of the invention are administered at the site of disease, e.g. at the site or near (e.g., about or at least 1, 2, 3, 4, 5, 6, 7, 8, 9, 10, 11, 12, 13, 14, 15, 16, 17, 18, 19, 20, 25, 30, 40, 50 millimeters from) the site of a disease lesion (e.g., vascular stenosis/blockage, necrotic tissue or site of gangrenous infection).

"A patient in need thereof" is referred to herein as a patient diagnosed with or suspected of having a disease amendable to stem cell therapy.

EXAMPLE

Reprogramming of human cord blood CD34+ cells or peripheral blood mononuclear cells with episomal plasmids and aluminum hydroxide under feeder free conditions.

This procedure generates human induced pluripotent stem cells (iPSCs) by reprogramming human cord blood CD34+ cells or PBMCs using episomal plasmids, Lonza 4D-Nucleofector™ system, Lonza #7 PSC medium and a human vitronectin matrix.

Materials used include: Human cord blood CD34+ cells (Lonza, Cat. No. 2C-101) or Human peripheral blood mononuclear cells (Lonza, Cat. No. CC-2702); Blood Cell Medium containing serum free basal medium, 50% IMDM (Invitrogen Cat No. 12440-053), 50% Ham's F12 (Invitrogen cat No. 11765054), 1× Chemically defined lipid concentration (Invitrogen Cat No. 11905-031), 1x Insulin-Transferrin-Selenium-X (ITS-X) (Invitrogen Cat No. 51500), 50 ug/mL Ascorbic acid (Sigma-Aldrich Cat No. 49752), 5 mg/mL Bovine Albumin Fraction V solution (Invitrogen Cat No. 15260-037), 2 mM GlutaMaxTM-I (Invitrogen Cat No. 35050) as well as cord blood-specific growth factors including 100 ng/mL Recombinant human SCF (Peprotech Cat No. AF-300-07), 100 ng/mL Recombinant human Flt3-ligand (Peprotech Cat No. AF-300-19), 20 ng/mL Recombinant human TPO (Peprotech Cat No. 300-18), and 10 ng/mL Recombinant human IL-3 (Peprotech Cat No. 200-03) as well as PBMC specific growth factors such as 200 μM 1-thioglycerol (Sigma #M6145), 100 μg/mL Holo-transferrin (R&D Systems #2914-HT), 1 μM Dexamethasone (Sigma #D1756), 100 ng/mL (PeproTech #300-07), 2U/mL EPO (R&D Systems #287-TC-500), 10 ng/mL IL-3 (PeproTech #200-03), and Alro 40 ng/mL IGF-1 (Peprotech #100-11). Also used are cGMP-grade pEB-C5 and pEB-Tg plasmids; alternatively pCE-OCT3/4, pCE-hSK, pCE-hUL, pCE-p53mDD, pCE-EBNA1, Alhydrogel 2% (Invitrogen vac-alu-50), Lonza #7 Pluripotent Stem Cell (PSC) medium, 0.4% Trypan Blue solution (Invitrogen cat No 15250061), 1×DPBS (Lonza Cat No. 17-512F), 1×DPBS++ (Lonza cat No 17-513F) and a P3 Primary Cell 4D-Nucleofector™ X Kit L (Lonza Cat No. V4XP-3012).

The Equipment used includes a Lonza 4D-Nucleofector™ system (Lonza Cat No. AAF-1001B, AAF-1001X), Humidified incubator at 37° C.±2° C. with 5% CO2±2%, 3.8% O2, Biohazard trash receptacle, Tissue culture hood, Hemocytometer, Microscope, 37° C. water bath, Centrifuge capable of 200×g with rotors for 15 mL tubes, Costar Stripette Paper-Wrapped Disposable Polystyrene Serological Pipets 10 mL (Thermofisher Cat No. 07-200-574), Costar Stripette Paper-Wrapped Disposable Polystyrene Serological Pipets 10 mL (Thermofisher Cat No. 07-200-573), Drummond Portable Pipet-Aid Filler/Dispensers XP (Thermofisher Cat No. 13-681-15E), Sterile Costar Microcentrifuge Tubes RNase free certified 1.7 mL Natural (ThermoFisher Cat No. 07-200-534), Sterile 1000 uL filter micropipette tip (Rainin Cat No. RT-1000F), Sterile 200 μL filter micropipette tip (Rainin Cat No. RT-200F), Sterile 20 μL filter micropipette tip (Rainin Cat No. RT-20F), Sterile 10 μL filter micropipette tip (Rainin Cat No. RT-10GF), Pipet-Lite XLS 1000 μL micropipette (Rainin Cat No. SL-STARTXLS), Pipet-Lite XLS 200 μL micropipette (Rainin Cat No. SL-STARTXLS), Pipet-Lite XLS 20 μL micropipette (Rainin Cat No. SL-STARTXLS), Pipet-Lite XLS with RFID 0.1-2 μL micropipette (Rainin Cat No. SL-2XLS), Corning 12-well tissue culture plate (Corning Cat No. 3513), 6-well tissue culture plate (ThermoFisher Cat No. 08-772-1B), Falcon 15 mL conical centrifuge tube (ThermoFisher Cat No. 14-959-70C).

On day 0, the procedure includes Cell Nucleofection as follows: Coat tissue culture plates (9.6 cm²/well) with lmL vitronectin at a concentration of 10 μg/mL. Allow coating to incubate 1 hour. Ensure Alhydrogel is evenly suspended by vortexing. Combine Alhydrogel and SFM at a ratio of 3 μL for each mL SFM. For each transfection sample, transfer 2 mL of SFM into 1 well of a 6-well plate. Put plate in 37° C. humidified incubator to pre-warm the medium. Collect human blood cells in a Falcon 15 mL conical tube. Take 10 µL of cell suspension and mix well with 10 µL of Trypan Blue. Count viable cells using a hemocytometer under a microscope. For each transfection sample, place $10^6$ viable cells in a new 15 mL tube and centrifuge cells at 200 g for five (5) minutes. Remove supernatant. Freeze cells quickly on dry ice and store at −80° C. for future STR analysis. Combine 82 µL P3 solution and 18 µL supplement from P3 Primary Cell 4D-Nucleofector™ X Kit L in a sterile microcentrifuge tube. Add pEB-C5: pEB-Tg or pCE-OCT3/4: pCE-hSK: pCE-hUL: pCE-p53mDD: pCE-EBNA1 plasmids at ratios of 8:2 or 0.63:0.63:0.63:0.63:0.5 µg respectively and mix well. Resuspend cells with pre-mixed Nucleofection™ Solution previously prepared. Mix well with micropipette and transfer to a Nucleofection™ cuvette (provided with kit). Nucleofect cells using 4D-Nucleofector™ using program EO-100. After Nucleofection, take 0.5 mL pre-warmed SFM and add into the cuvette using micropipette in the tissue culture hood. Then use a transfer pipet provided with the Nucleofection™ kit to transfer the cells to the pre-warmed SFM in 1 well of 6-well plate. Place plate into a humidified incubator.

On day 2 the procedure is as follows: Dilute 40 µL of 250 µg/mL vitronectin into 1 mL of 1×DPBS$^{++}$ and add into 1 well of 6-well plate. Coat the plate in an incubator for three (3) hours. Transfer Nucleofected CD34+ cells into one 15 mL tube and centrifuge cells at 200 g for five (5) minutes. Remove the medium and resuspend cells in 2 mL Lonza #7 medium. Add 0.2 uL of 10 uM A8301 (f.c. 1 µM) into the cell suspension. Aspirate off vitronectin from the well and seed cells into it. Put the plate into the incubator.

On days 2 and 4 the procedure involves the following steps: Every other day add 1.5 mL L7 until well volume exceeds 5 mL.

On day 6 the procedure is as follows: When well volume exceeds 6 mL, aspirate the supernatant leaving behind an approximate volume of 1 mL medium. Gently handle culture so as not to disturb the cells covering the bottom of the well. Add 1.5 mL Lonza #7 PSC medium.

Repeat the procedures from Days 2, 4 and 6 until colonies appear roughly between days 14 to 18.

On day 16, prepare 24-well vitronectin-coated plates.

On days 18 to 20 the procedure involves colony picking steps as follows: Aspirate vitronectin coating from 12-well plate. To empty wells, add 250 µL L7 Medium. Under phase microscope, mark colonies for picking based on morphology. Conduct the following steps one colony at a time. Under dissecting scope, scrape colonies from the surface of the well with a micropipette tip. Draw colony into micropipette tip into roughly 30 µL of volume. Transfer colony into 24-well plate. After colonies have been collected, place 24-well plate into a humidified, 5% $CO_2$, 20% $O_2$, 37° C. incubator.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. An in vitro method of enhancing nuclear reprogramming of a human somatic cell, the method comprising: contacting a population of-human somatic cells with (a) an effective dose of an aluminum composition; and (b) a cocktail of reprogramming factors; for a period of time sufficient to reprogram the human somatic cells to induced pluripotent stem cells, wherein the aluminum composition is selected from the group consisting of aluminum hydroxide, aluminum phosphate and aluminum sulfate.

2. The method of claim 1, wherein the aluminum composition and reprogramming factors are provided sequentially or simultaneously.

3. The method of claim 1, wherein the aluminum composition is aluminum hydroxide.

4. The method of claim 3, wherein the effective dose of aluminum hydroxide is about or at least 40-80 micrograms/ml.

5. The method of claim 1, wherein the aluminum composition is aluminum phosphate.

6. The method of claim 1, wherein the aluminum composition is aluminum sulfate.

7. The method of claim 1, wherein the cocktail of reprogramming factors comprises the use of nucleic acids encoding Oct4, Sox2, Lin28, and Nanog, or corresponding cell permeant peptides of the same, and the cells are reprogrammed to pluripotency.

8. The method of claim 1, wherein the cocktail of reprogramming factors comprises the use of nucleic acids encoding Oct4, Sox2, c-Myc, and KLF4, or corresponding cell permeant peptides of the same, and the cells are reprogrammed to pluripotency.

9. The method of claim 1, wherein the human somatic cell type is peripheral blood mononuclear cell (PBMC), cord blood mononuclear cells, or fibroblasts.

10. The method of claim 1, wherein the reprogramming factors are provided as cell permeant proteins.

11. The method of claim 1, wherein the reprogramming factors are provided as nucleic acids encoding the proteins.

12. The method of claim 1, resulting in a nuclear reprogramming efficiency wherein the nuclear reprogramming efficiency is greater than if the method was carried out without the aluminum composition.

13. The method of claim 12 wherein the nuclear reprogramming efficiency is about 1 to about 5 fold greater with respect to the expression of at least one key pluripotency marker.

14. The method of claim 12 wherein the nuclear reprogramming efficiency is about 1 to about 5 fold greater with respect to an amount of the induced pluripotent stem cells produced.

* * * * *